United States Patent
Goormachtig et al.

(10) Patent No.: US 11,071,302 B2
(45) Date of Patent: Jul. 27, 2021

(54) MEANS AND METHODS FOR PLANT YIELD ENHANCEMENT

(71) Applicants: APHEA.BIO NV, Zwijnaarde (BE); FUNDACIÓN CENTRO DE EXCELENCIA EN INVESTIGACIÓN DE MEDICAMENTOS INNOVADORES EN ANDALUCÍA, MEDINA, Granada (ES)

(72) Inventors: Sofie Goormachtig, Ghent (BE); Tom Viaene, Ghent (BE)

(73) Assignee: Aphea.Bio NV, Zwijnaarde (BE)

( * ) Notice: Subject to any disclaimer, the term of this patent is extended or adjusted under 35 U.S.C. 154(b) by 224 days.

(21) Appl. No.: 16/338,378

(22) PCT Filed: Oct. 2, 2017

(86) PCT No.: PCT/EP2017/074969
§ 371 (c)(1),
(2) Date: Mar. 29, 2019

(87) PCT Pub. No.: WO2018/060519
PCT Pub. Date: Apr. 5, 2018

(65) Prior Publication Data
US 2020/0022374 A1 Jan. 23, 2020

(30) Foreign Application Priority Data

Sep. 30, 2016 (EP) .................................... 16191812
Sep. 30, 2016 (EP) .................................... 16191840
Sep. 30, 2016 (EP) .................................... 16191876
Dec. 23, 2016 (EP) .................................... 16206646
Dec. 23, 2016 (EP) .................................... 16206653
Dec. 23, 2016 (EP) .................................... 16206657

(51) Int. Cl.
*C12R 1/465* (2006.01)
*A01N 63/10* (2020.01)
*C12N 1/20* (2006.01)
*C12R 1/06* (2006.01)

(52) U.S. Cl.
CPC ............... *A01N 63/10* (2020.01); *C12N 1/20* (2013.01); *C12R 1/06* (2013.01); *C12R 1/465* (2013.01)

(58) Field of Classification Search
CPC ............ C12N 1/20; C12R 1/465; A01N 63/00
See application file for complete search history.

(56) References Cited

FOREIGN PATENT DOCUMENTS

| WO | WO 2009/115822 A1 | 9/2009 |
| WO | WO 2013/040366 A1 | 3/2013 |
| WO | WO 2014/201044 A2 | 12/2014 |
| WO | WO 2015/199541 A1 | 12/2015 |

OTHER PUBLICATIONS

Mages et al. Identities of *arthrobacter* spp. and *arthrobacter*-Like Bacteria Encountered in Human Clinical Specimens. Journal of Clinical microbiology. 2008;46(9):2980-2986.*
International Search Report and Written Opinion received in PCT Application No. PCT/EP2017/074969 dated Jan. 10, 2018.
I.S. Mages et al., "Identities of *arthrobacter* spp. and *arthrobacter*-Like Bacteria Encountered in Human Clinical Specimens," Journal of Clinical Microbiology, vol. 46, No. 9, Jul. 2008, pp. 2980-2986.
Liu Qing et al., "High Diversity and Distinctive Community Structure of Bacteria on Glaciers in China revealed by 454 Pyrosequencing," Systematic and Applied Microbiology, vol. 38, No. 8, 2015, pp. 578-585.
Monica Rosenblueth et al., "Bacterial Endophytes and Their Interactions with Hosts," Molecular Plant-Microbe Interactions, vol. 19, No. 8, 2006, pp. 827-837.

* cited by examiner

*Primary Examiner* — Lynn Y Fan
(74) *Attorney, Agent, or Firm* — Knobbe, Martens, Olson & Bear LLP

(57) ABSTRACT

The present invention relates to the field of sustainable agriculture. Specifically, the invention provides microbial compositions and methods useful for the production of crop plants. In particular, the compositions and methods disclosed herein are useful for enhancing plant growth.

6 Claims, 12 Drawing Sheets

Figure 1:
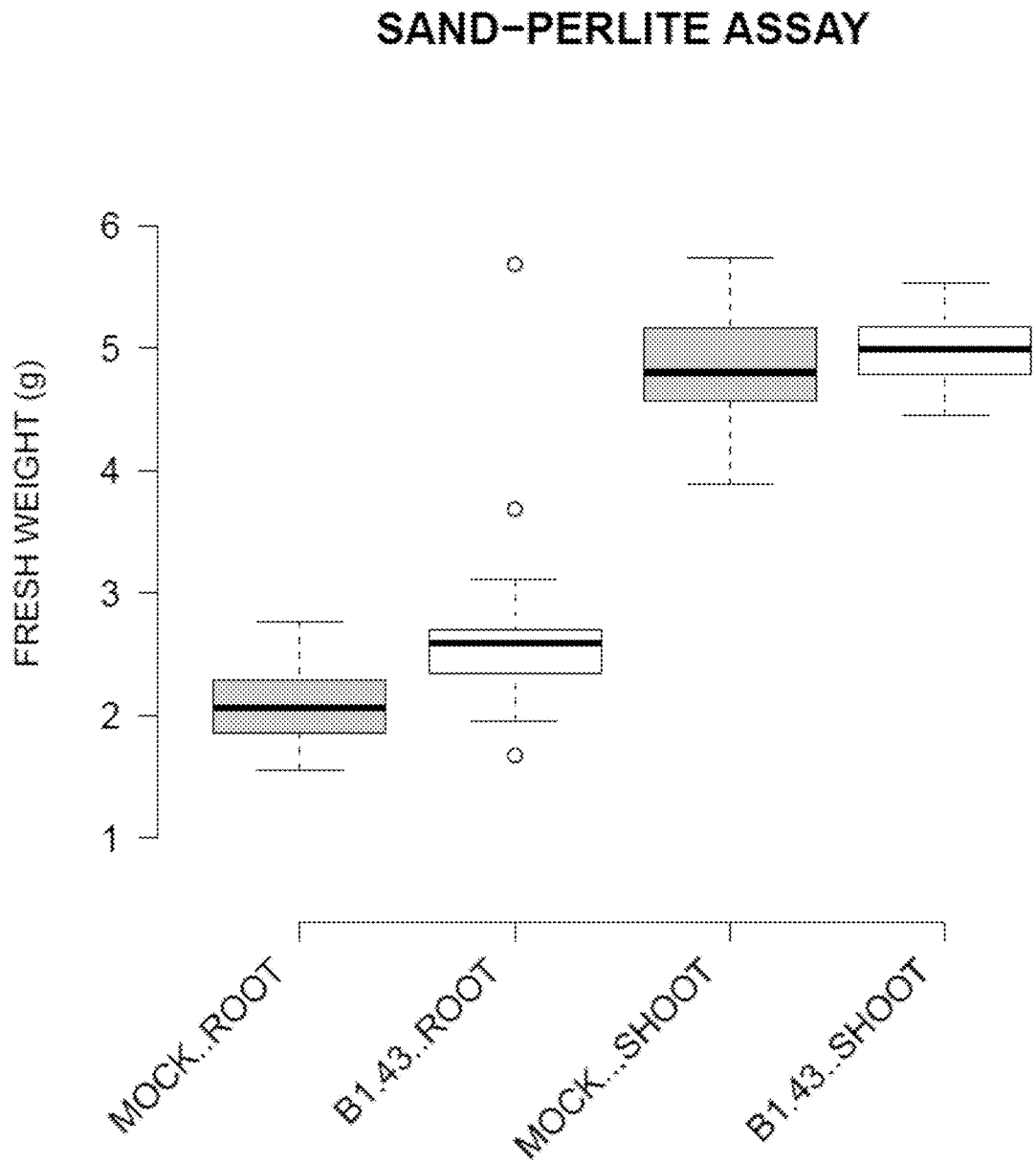

Specification includes a Sequence Listing.

MEANS AND METHODS FOR PLANT YIELD ENHANCEMENT

CROSS-REFERENCED TO RELATED APPLICATIONS

This application is a U.S. National Phase Application of PCT International Application No. PCT/EP2017/074969, filed on Oct. 2, 2017, designating the United States of America and published in the English as WO 2018/060519 on Apr. 5, 2018, which claims priority to European Application No. 16191876.8, filed Sep. 30, 2016; European Application No. 16191840.4, filed Sep. 30, 2016; European Application No. 16191812.3, filed Sep. 30, 2016; European Application No. 16206657.5, filed Dec. 23, 2016; European Application No. 16206646.8, filed Dec. 23, 2016; and European Application No. 16206653.4, filed Dec. 23, 2016; the entire contents of which are incorporated herein by reference.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 30229868 1.TXT, the date of creation of the ASCII text file is Mar. 29, 2019, and the size of the ASCII text file is 5.98 KB.

TECHNICAL FIELD

The present invention relates to the field of sustainable agriculture. Specifically, the invention provides microbial compositions and methods useful for the production of crop plants. In particular, the compositions and methods disclosed herein are useful for enhancing plant growth and/or plant yield.

BACKGROUND

Agriculture in developed countries has become increasingly dependent on chemical fertilizers and pesticides in order to achieve and/or main high crop yields. Given the negative environmental impact of some of these agricultural aids, there is a growing interest to improve crop yield using eco-friendly and more sustainable approaches. In recent years, several technical and technological innovations were proposed in order to improve the sustainability of production systems, through a significant reduction of agrochemicals. A promising practice is the use of substances and/or microorganisms that enhance plant growth, increase tolerance to unfavorable soil and/or environmental conditions, and/or improve the resource use efficiency. The diversity of microorganisms in the soil is huge and a few grams of soil contain already hundred millions to billion microorganisms. Bacteria are the most abundant microbes in soil followed by fungi.

However, since many microorganisms can be a source of plant diseases, it is not obvious to identify microorganisms that live closely associated with the root system of crops in a mutualistic way, supporting the plant's growth and vigor. The non-pathogenic and plant growth beneficial bacteria that colonize the rhizosphere are often referred to as plant-growth-promoting rhizobacteria (PGPR). PGPR can confer diverse beneficial effects to the plant. Several bacteria have been disclosed that increase plant growth and/or reduce susceptibility to diseases caused by fungi, bacteria, viruses or other plant pathogens (e.g. Compant et al 2005, Applied and Environmental Microbiology 71: 4951-4959; Singh et al 2011, Agriculture, Ecosystems and Environment 140: 339-353). Other PGPR act as elicitors of tolerance to abiotic stresses, such as drought, salt and nutrient deficiency (Yang et al 2009 Trends in Plant Science 14:1-4).

Plant growth promotion is a complex phenomenon rarely attributable to a single mechanism as most PGP microbes influence plant growth through multiple mechanisms, and in some cases their PGP effect may only occur through interactions with other microbes (Pereg and McMillan 2015, Soil Biology and Biochemistry, 80: 349-358). Moreover, any microbial agent added to the rhizosphere has to interact not only with the plant but also with any other organism sharing the same ecological niche. To be successful the inoculant has to maintain a critical population mass in the soil, outcompete other microbes for resources and have the right conditions to exert its beneficial activity (Pereg and McMillan 2015, Soil Biology and Biochemistry 80: 349-358). In case of biocontrol, the PGPR even have to suppress pathogens. In this application a bacterial collection was screened for PGPR using wheat and corn plants. Several candidates were identified which promote plant growth and development.

SUMMARY

Applicants have identified isolated bacterial strains as well as combinations of the latter that effectively promotes plant growth and plant yield.

To administer microorganisms to plants, it is advisable to formulate the microorganisms in a combination. This combination can also comprise other biologicals or agrochemicals to stimulate plant growth. Therefore, in another embodiment, a combination is provided comprising an agriculturally compatible carrier and an embodiment of the bacterial culture of current invention. In another embodiment, a combination is provided comprising an agriculturally compatible carrier and the bacterial culture according to an embodiment of the current invention. In another embodiment, a plant seed coated with an embodiment of the bacterial culture of current invention is provided.

Another aspect of the invention is the use of the bacterial culture of current invention to enhance plant yield and/or plant growth. In one embodiment, the bacterial culture of current invention is provided to increase nutrient uptake and/or nutrient use efficiency of a plant. In another embodiment, the bacterial culture of current invention is provided to increase the nitrogen fixating capacities of a plant.

Yet another aspect of the invention is a method for enhancing growth and/or yield of a plant, wherein said method comprises:
  inoculating a plant growth medium with the bacterial culture of current invention;
  growing a plant in said plant growth medium;
to enhance growth and/or yield of said plant.

In another embodiment, the bacterial cultures of the above provided methods are applied to the plant growth medium as a powder, as a pellet, as a granule, as a liquid. Another aspect of the invention is a method for enhancing growth and/or yield of a plant, said method comprising growing coated seeds of a plant, wherein said seeds are coated with an embodiment of the bacterial population of current invention, to obtain enhanced growth and/or yield of said plant.

In yet another embodiment, a method is provided for enhancing growth and/or yield of a plant comprising:
  growing a plant in an environment that supports plant growth;

administering a sprayable formulation to said environment or to said plant, said formulation comprising the bacterial culture of current invention;

to obtain enhanced growth and/or yield of said plant.

Deposit of Biological Material

Purified cultures of the microbial strain described in the present application were deposited at the BCCM (Belgian Coordinated Collections of Microorganisms) consortium (BCCM represented by Laboratorium voor Microbiologie—Bacterienverzameling (LMG), Universiteit Gent, K. L. Ledeganckstraat 35, 9000 Gent, Belgium), recognized as an International Depositary Authority by the World Intellectual Property organization since Mar. 1, 1992 and in accordance with the Budapest Treaty as specified in Rule 31(1) EPC2000 for the purpose of patent procedure and the regulations thereunder. Accession number for the *S. niveus* strain deposit is *Streptomyces niveus* CA-227571=LMG P-29828 (deposited on Sep. 19, 2016) and for the *A. oxydans* strain deposit is *Arthrobacter oxydans* CB-278407=LMG P-29827 (deposited on Sep. 19, 2016).

The *Arthrobacter agilis* strain can be obtained from the Microbial Strain Collection of Fundacion MEDINA in Spain with accession number CB-283399 CAJA 1-24.

BRIEF DESCRIPTION OF THE DRAWINGS

FIG. 1. Merged repeats in sand-perlite assay for strain CA-227571. Root and shoot fresh weights (g) are shown for mock and treated CA-227571 (or B1.43) maize seedlings.

FIG. 2. Merged repeats in sand-perlite assay for strain CB-278407. Root and shoot fresh weights (g) are shown for mock and treated CB-278407 (or CAJA1.6) maize seedlings.

FIG. 3. Merged repeats in maize field soil screening for strain CA-227571. Root and shoot fresh weights (g) are shown for mock and treated CA-227571 (or VIB1.43) maize seedlings.

FIG. 4. Results for maize phenovision screening for strain CA-227571. Root and shoot fresh weights (g) are shown for mock and treated CA-227571 (or VIB1.43) maize seedlings.

FIG. 5. Results for maize phenovision screening for strain CA-227571. Leaf 3 and Leaf 4 lengths (cm) are shown for mock and treated CA-227571 (or VIB1.43) maize seedlings.

FIG. 6. Merged repeats in wheat soil assay for strain CA-227571. Root and shoot fresh weights (g) are shown for mock and treated CA-227571 (or VIB1.43) wheat seeds.

FIG. 7. Results for maize phenovision screening for strain CB-278407. Root and shoot fresh weights (g) are shown for mock and treated CB-278407 (or CAJA1.6) maize seedlings.

FIG. 8. Results for maize phenovision screening for strain CB-278407. Leaf 3 and Leaf 4 lengths (cm) are shown for mock and treated CB-278407 (or CAJA1.6) maize seedlings.

FIG. 9. Merged repeats in wheat soil assay for strain CB-278407. Root and shoot fresh weights (g) are shown for mock and treated CB-278407 (or CAJA1.6) wheat seeds.

FIG. 10. Merged repeats in wheat soil assay for the combination of strains CB-278407 (strain 1-6, *Arthrobacter oxydans*) and CA-227571 (strain 1-43, *Streptomyces niveus*). Leaf 2 lengths (cm) are shown for mock and treated (strain 1-6, strain 1-43 and the combination strain 1-43 and 1-6) wheat seeds.

FIG. 11: Results for wheat greenhouse soil assay for the combination of strains CA-227571 (strain 1-43, *Streptomyces niveus*) and CB-283399 (strain 1-24, *Arthrobacter agilis*). Plant height for the non-treated (none), mock-treated (M) or bacteria-treated (strain 1-24 or combination strain 1-24 and 1-43) with 90% confidence intervals.

FIG. 12: Results for wheat greenhouse soil assay for the combination of strains CA-227571 (strain 1-43, *Streptomyces niveus*) and CB-283399 (strain 1-24, *Arthrobacter agilis*). Dry weight (biomass) for the non-treated (none), mock-treated (M) or bacteria-treated (strain 1-24 or combination strain 1-24 and 1-43) with 90% confidence intervals.

DETAILED DESCRIPTION

Definitions

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, N.Y. (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

Diverse plant-associated microorganisms can positively impact plant health and physiology in a variety of ways. In the current application, it is demonstrated that an enriched bacterial culture comprising the strains or a combination of strains according to the description below have a surprising promoting effect on plant growth and development. Such beneficial microorganisms with plant growth promoting activity are generally referred to as plant growth promoting microorganisms.

The term "plant growth promoting activity" as used herein, encompasses a wide range of improved plant properties, including but not limiting to increased root development, increased leaf area, increased plant yield, increased seed germination, increased photosynthesis, increase in accumulated biomass of the plant, increased nitrogen fixation or increased efficiency of nutrients such as nitrogen, phosphorus or potassium. In various embodiments of this second aspect, the increase or improvement is an at least 5% increase or at least 10% increase or at least 25% increase or at least 50% increase or at least 75% increase or at least a 100% increase in the property being measured. Thus, as non-limiting examples, the microbial population comprising one or more strains of the current application may produce an above stated percentage increase in nitrogen fixation, or an above stated increase in total root weight, or in leaf area or in plant product yield, or an above stated percentage increased accumulated biomass of the plant.

The strains of current application are soil bacteria mostly present in the rhizosphere and in close contact with the root system of plants. The term "rhizosphere" is used interchangeably with "root zone" to denote that segment of the soil that surrounds the roots of a plant and is influenced by them. The strains of the current application are able to colonize the plant externally but also internally and can also be considered as an "endophyte".

The term "plant" encompasses whole plants and plant parts, including seeds, shoots, stems, leaves, roots (including tubers), bulbs, buds, flowers, and tissues and organs. The term "plant" also encompasses plant cells, suspension cultures, callus tissue, embryos, meristematic regions, gametophytes, sporophytes, pollen and microspores.

The term "endophyte" as used herein is a symbiont that lives within a plant for at least part of its life without causing apparent disease. Endophytes may be transmitted either vertically (directly from parent to offspring) or horizontally (from individual to unrelated individual).

The term "bacterium" or "bacteria" includes any prokaryotic organism that does not have a distinct nucleus. While being both part of the group of microorganisms, bacteria and fungi are clearly distinct.

The term "fungi" or "fungus" includes a wide variety of nucleated spore-bearing organisms that are devoid of chlorophyll. Examples of fungi include yeasts, molds, mildews, rusts and mushrooms.

The "plant's root system" refers to the belowground parts of a plant, comprising the primary root, secondary roots, adventitious roots, lateral roots, root hairs.

Plants that are particularly useful in the current invention include in particular monocotyledonous and dicotyledonous plants including fodder or forage legumes, ornamental plants, food crops, trees or shrubs selected from the list comprising Acer spp., Actinidia spp., Abelmoschus spp., Agave sisalana, Agropyron spp., Agrostis stolonifera, Allium spp., Amaranthus spp., Ammophila arenaria, Ananas comosus, Annona spp., Apium graveolens, Arachis spp, Artocarpus spp., Asparagus officinalis, Avena spp. (e.g. Avena sativa, Avena fatua, Avena byzantina, Avena fatua var. sativa, Avena hybrida), Averrhoa carambola, Bambusa sp., Benincasa hispida, Bertholletia excelsea, Beta vulgaris, Brassica spp. (e.g. Brassica napus, Brassica rapa ssp. [canola, oilseed rape, turnip rape]), Cadaba farinosa, Camellia sinensis, Canna indica, Cannabis sativa, Capsicum spp., Carex elata, Carica papaya, Carissa macrocarpa, Carya spp., Carthamus tinctorius, Castanea spp., Ceiba pentandra, Cichorium endivia, Cinnamomum spp., Citrullus lanatus, Citrus spp., Cocos spp., Coffea spp., Colocasia esculenta, Cola spp., Corchorus sp., Coriandrum sativum, Corylus spp., Crataegus spp., Crocus sativus, Cucurbita spp., Cucumis spp., Cynara spp., Daucus carota, Desmodium spp., Dimocarpus longan, Dioscorea spp., Diospyros spp., Echinochloa spp., Elaeis (e.g. Elaeis guineensis, Elaeis oleifera), Eleusine coracana, Eragrostis tef, Erianthus sp., Eriobotrya japonica, Eucalyptus sp., Eugenia uniflora, Fagopyrum spp., Fagus spp., Festuca arundinacea, Ficus carica, Fortunella spp., Fragaria spp., Ginkgo biloba, Glycine spp. (e.g. Glycine max, Soja hispida or Soja max), Gossypium hirsutum, Helianthus spp. (e.g. Helianthus annuus), Hemerocallis fulva, Hibiscus spp., Hordeum spp. (e.g. Hordeum vulgare), Ipomoea batatas, Juglans spp., Lactuca sativa, Lathyrus spp., Lens culinaris, Linum usitatissimum, Litchi chinensis, Lotus spp., Luffa acutangula, Lupinus spp., Luzula sylvatica, Lycopersicon spp. (e.g. Lycopersicon esculentum, Lycopersicon lycopersicum, Lycopersicon pyriforme), Macrotyloma spp., Malus spp., Malpighia emarginata, Mammea americana, Mangifera indica, Manihot spp., Manilkara zapota, Medicago sativa, Melilotus spp., Mentha spp., Miscanthus sinensis, Momordica spp., Morus nigra, Musa spp., Nicotiana spp., Olea spp., Opuntia spp., Ornithopus spp., Oryza spp. (e.g. Oryza sativa, Oryza latifolia), Panicum miliaceum, Panicum virgatum, Passiflora edulis, Pastinaca sativa, Pennisetum sp., Persea spp., Petroselinum crispum, Phalaris arundinacea, Phaseolus spp., Phleum pratense, Phoenix spp., Phragmites australis, Physalis spp., Pinus spp., Pistacia vera, Pisum spp., Poa spp., Populus spp., Prosopis spp., Prunus spp., Psidium spp., Punica granatum, Pyrus communis, Quercus spp., Raphanus sativus, Rheum rhabarbarum, Ribes spp., Ricinus communis, Rubus spp., Saccharum spp., Salix sp., Sambucus spp., Secale cereale, Sesamum spp., Sinapis sp., Solanum spp. (e.g. Solanum tuberosum, Solanum integrifolium or Solanum lycopersicum), Sorghum bicolor, Spinacia spp., Syzygium spp., Tagetes spp., Tamarindus indica, Theobroma cacao, Trifolium spp., Tripsacum dactyloides, Triticosecale rimpaui, Triticum spp. (e.g. Triticum aestivum, Triticum durum, Triticum turgidum, Triticum hybernum, Triticum macha, Triticum sativum, Triticum monococcum or Triticum vulgare), Tropaeolum minus, Tropaeolum majus, Vaccinium spp., Vicia spp., Vigna spp., Viola odorata, Vitis spp., Zea mays, Zizania palustris, Ziziphus spp., amongst others. In a preferred embodiment, said plants are wheat or corn.

An "effective amount" refers to an amount sufficient to effect beneficial or desired results. In a non-limiting example, an "effective amount" leads to a statistically significant increase of plant growth and/or biomass and/or yield as compared to the growth, biomass and/or yield of the control plant. An effective amount can be administered in one or more administrations. A "control plant" as used in current application provides a reference point for measuring changes in phenotype of the subject plant and may be any suitable plant cell, seed, plant component, plant tissue, plant organ or whole plant. A control plant may comprise for example a plant or cell which is genetically identical to the subject plant or cell but which is not exposed to the same treatment (e.g. administration of one or more strains of the current invention) as the subject plant or cell.

The "plant's surroundings" refer to the plant growth medium which is accessible by the plant to absorb water and nutrients. For soil, there are the soil particles around the root, including the rhizosphere; for hydroculture, this is the soilless medium or aquatic based environment where plant roots can tap into; for in vitro culture, this is the synthetic medium in the used recipient.

The terms "stimulating", "enhancing", "increasing" or "improving" refers to an at least 5% increase or at least 10% increase or at least 25% increase or at least 50% increase or at least 75% increase or at least a 100% increase in the property being measured (e.g. plant growth, plant yield).

"Yield" as used herein, generally refers to a measurable product from a plant, and more particularly to the amount of harvestable plant material or plant-derived product. "Yield" is normally defined as the measurable produce of economic value of a crop. For crop plants, "yield" also means the amount of harvested material per hectare or unit of production. Yield may be defined in terms of quantity or quality. The harvested material may vary from crop to crop, for example, it may be seeds, above ground biomass, roots, fruits, cotton fibres, any other part of the plant, or any plant-derived product which is of economic value. The term "yield" also encompasses yield potential, which is the maximum obtainable yield. Yield may be dependent on a number of yield components, which may be monitored by certain parameters. These parameters are well known to persons skilled in the art and vary from crop to crop. The yield can be determined using any convenient method, for example, kilograms of plant product produced per hectare of planting or bushels or pound of plant product produced per acre of planting. The term "yield" also encompasses harvest index, which is the ratio between the harvested biomass over the total amount of biomass. Yield and yield increase (in comparison to a control plant) can be measured in a number of ways, and it is understood that a skilled person will be able to apply the correct meaning in view of the particular embodiments, the particular crop concerned and the specific purpose or application concerned. The terms "enhanced yield" or "improved yield" or "increased yield" can be used interchangeable. As used herein, the term "enhanced yield" means any improvement in the yield of any measured plant product, such as grain, fruit, leaf, root, cob or fiber. In accordance with the invention, changes in different phenotypic traits may improve yield. For example, and without limitation, parameters such as floral organ development, root initiation, root biomass, seed number, seed weight, harvest index, leaf formation, phototropism, apical dominance, and fruit development, are suitable measurements of improved yield. Increased yield includes higher fruit yields, higher seed yields, higher fresh matter production, and/or higher dry matter production. Any increase in yield is an improved yield in accordance with the invention. For example, the improvement in yield can comprise a 0.1%, 0.5%, 1%, 3%, 5%, 10%, 15%, 20%, 30%, 40%, 50%, 60%, 70%, 80%, 90% or greater increase in any measured parameter. For example, an increase in the bushels/acre yield of wheat or corn derived from a crop comprising plants which are treated with the plant growth promoting bacteria of the invention, as compared with the bushels/acre yield from untreated wheat or corn cultivated under the same conditions, is an improved yield in accordance with the invention. The increased or improved yield can be achieved in the absence or presence of stress conditions. For example, enhanced or increased "yield" refers to one or more yield parameters selected from the group consisting of biomass yield, dry biomass yield, aerial dry biomass yield, underground dry biomass yield, fresh-weight biomass yield, aerial fresh-weight biomass yield, underground fresh-weight biomass yield; enhanced yield of harvestable parts, either dry or fresh-weight or both, either aerial or underground or both; enhanced yield of crop fruit, either dry or fresh-weight or both, either aerial or underground or both; and enhanced yield of seeds, either dry or fresh-weight or both, either aerial or underground or both. "Crop yield" is defined herein as the number of bushels of relevant agricultural product (such as grain, forage, or seed) harvested per acre. Crop yield is impacted by abiotic stresses, such as drought, heat, salinity, and cold stress, and by the size (biomass) of the plant. The yield of a plant can depend on the specific plant/crop of interest as well as its intended application (such as food production, feed production, processed food production, biofuel, biogas or alcohol production, or the like) of interest in each particular case. Thus, in one embodiment, yield can be calculated as harvest index (expressed as a ratio of the weight of the respective harvestable parts divided by the total biomass), harvestable parts weight per area (acre, square meter, or the like); and the like. The harvest index is the ratio of yield biomass to the total cumulative biomass at harvest. Harvest index is relatively stable under many environmental conditions, and so a robust correlation between plant size and grain yield is possible. Measurements of plant size in early development, under standardized conditions in a growth chamber or greenhouse, are standard practices to measure potential yield advantages conferred by the presence of plant growth promoting bacteria. Accordingly, the yield of a plant can be increased by improving one or more of the yield-related phenotypes or traits. Such yield-related phenotypes or traits of a plant the improvement of which results in increased yield comprise, without limitation, the increase of the intrinsic yield capacity of a plant, improved nutrient use efficiency, and/or increased stress tolerance. For example, yield refers to biomass yield, e.g. to dry weight biomass yield and/or fresh-weight biomass yield. Biomass yield refers to the aerial or underground parts of a plant, depending on the specific circumstances (test conditions, specific crop of interest, application of interest, and the like). In one embodiment, biomass yield refers to the aerial and underground parts. Biomass yield may be calculated as fresh-weight, dry weight or a moisture adjusted basis. Biomass yield may be calculated on a per plant basis or in relation to a specific area (e.g. biomass yield per acre/square meter/or the like). "Yield" can also refer to seed yield which can be measured by one or more of the following parameters: number of seeds or number of filled seeds (per plant or per area (acre/square meter/or the like)); seed filling rate (ratio between number of filled seeds and total number of seeds); number of flowers per plant; seed biomass or total seeds weight (per plant or per area (acre/square meter/or the like); thousand kernel weight (TKW; extrapolated from the number of filled seeds counted and their total weight; an increase in TKW may be caused by an increased seed size, an increased seed weight, an increased embryo size, and/or an increased endosperm). Other parameters allowing to measure seed yield are also known in the art. Seed yield may be determined on a dry weight or on a fresh weight basis, or typically on a moisture adjusted basis, e.g. at 15.5 percent moisture. For example, the term "increased yield" means that a plant, exhibits an increased growth rate, e.g. in the absence or presence of abiotic environmental stress, compared to the corresponding wild-type plant. An increased growth rate may be reflected inter alia by or confers an increased biomass production of the whole plant, or an increased biomass production of the aerial parts of a plant, or by an increased biomass production of the underground parts of a plant, or by an increased biomass production of parts of a plant, like stems, leaves, blossoms, fruits, and/or seeds. A prolonged growth comprises survival and/or continued growth of the plant, at the moment when the untreated control plant shows visual symptoms of deficiency and/or death. When the plant treated with the PGPR of the application is a corn plant, increased yield for corn plants means, for example, increased seed yield, in particular for corn varieties used for feed or food. Increased seed yield of corn refers to an increased kernel size or weight, an increased kernel per ear, or increased ears per plant. Alternatively or in addition the cob yield may be increased, or the length or size of the cob is increased, or the kernel per cob ratio is improved. When the plant treated with the PGPR of the application is wheat, increased yield for wheat means, for example, increased seed yield. Increased seed yield of wheat refers to an increased kernel size, an increased kernel filling, increased thousand kernel weight, an increased kernel per ear, an increased grain yield per plant, or increased ears per plant. Alternatively or in addition the ear yield may be increased, or the length or size of the ear is increased, or the seeds per ear ratio is improved. When the plant treated with the PGPR of the application is a soy plant, increased yield for soy plants means increased seed yield, in particular for soy varieties used for feed or food. Increased seed yield of soy refers for example to an increased kernel size or weight, an increased kernel per pod, or increased pods per plant. When the plant treated with the PGPR of the application is an oil seed rape (OSR) plant, increased yield for OSR plants means increased seed yield, in particular for OSR varieties used for feed or food. Increased seed yield of OSR refers to an increased seed size or weight, an increased seed number per silique, or increased siliques per plant. When the plant treated with the PGPR of the application is a cotton plant, increased yield for cotton plants means increased lint yield. Increased lint yield of cotton refers in one embodiment to an increased length of lint. When the plant treated with the PGPR of the application is a plant belonging to grasses an increased leaf can mean an increased leaf biomass. Said increased yield can typically be achieved by enhancing or improving, one or more yield-related traits of the plant. Such yield-related traits of a plant comprise, without limitation, the increase of the intrinsic yield capacity of a plant, improved nutrient use efficiency, and/or increased stress tolerance, in particular increased abiotic stress tolerance. Intrinsic yield capacity of a plant can be, for example, manifested by improving the specific (intrinsic) seed yield (e.g. in terms of increased seed/grain size, increased ear number, increased seed number per ear, improvement of seed filling, improvement of seed composition, embryo and/or endosperm improvements, or the like); modification and improvement of inherent growth and development mechanisms of a plant (such as plant height, plant growth rate, pod number, pod position on the plant, number of internodes, incidence of pod shatter, efficiency of nodulation and nitrogen fixation, efficiency of carbon assimilation, improvement of seedling vigour/early vigour, enhanced efficiency of germination (under stressed or non-stressed conditions), improvement in plant architecture, cell cycle modifications, photosynthesis modifications, various signaling pathway modifications, modification of transcriptional regulation, modification of translational regulation, modification of enzyme activities, and the like); and/or the like. The term "isolated" means that the strain has been removed from its natural environment. "Isolated" thus implies a purification step. However, "isolated" does not necessarily reflect the extent to which the microorganism has been purified. The strains comprising the 16S rRNA sequence depicted in SEQ ID N° 1 or N° 2 or the strains of the current application are purified at least 2×, at least 5×, at least 10×, at least 50× or at least 100× from the raw material from which it is isolated. As a non-limiting example, if a microorganism is isolated from soil as raw material, the microorganism can be isolated to an extent that its concentration in a given quantity of purified or partially purified material (e.g. soil) is at least 2×, at least 5×, at least 10×, at least 50× or at least 100× that in the original raw material.

The term "sequence identity" as used herein refers to the extent that sequences are identical on a nucleotide-by-nucleotide basis over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. A gap, i.e., a position in an alignment where a residue is present in one sequence but not in the other is regarded as a position with non-identical residues. Determining the percentage of sequence identity can be done manually, or by making use of computer programs that are available in the art. Examples of useful algorithms are PILEUP. Software for performing BLAST analyses is publicly available through the National Center for Biotechnology Information (http://www.ncbi.nlm.nih.gov/). In order to reconstruct the evolutionary relationships and sequence identity of one bacterial isolate to another, phylogenetic approaches are used standardly exploiting the 16S rRNA sequence or a portion of the 16S rRNA sequence of the bacteria, although any other sequence or the entire genome of the microorganisms to be analyzed can also be used.

In microbiology, "16S rRNA sequence" refers to the sequence derived by characterizing the nucleotides that comprise the 16S ribosomal RNA gene(s). The bacterial 16S rRNA is approximately 1500 nucleotides in length.

The term "composition" as used herein is intended to mean a combination of an active agent (for this application this can be the (combination of) strains of the current invention, or an extract of its culture, or the supernatant of its culture, or one or more products derived from the strains of the current invention) and at least another compound which can be inert (e.g. a detectable agent or label or liquid carrier) or active (e.g. a fertilizer).

Non-limiting examples of said composition in practice are soluble powders, wettable granules, dry flowables, aqueous flowables, wettable dispersible granules, emulsifiable concentrates, aqueous suspensions, a fertilizer granule, a sprayable formulation, an agrochemical formulation. Thus, in another embodiment, an agrochemical composition comprising the A. oxydans strain of the current application is provided. This agrochemical composition can include a fertilizer, a micronutrient fertilizer material, an insecticide, a herbicide, a plant growth amendment, a fungicide, a molluscicide, an algicide, a bacterial inoculant, a fungal inoculant, or a combination thereof. In some cases the fertilizer is a liquid fertilizer. Liquid fertilizer can include without limitation, ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, hampene (chelated iron), dolomitic limestone, hydrate lime, calcium carbonate, diammonium phosphate, monoammonium phosphate, potassium nitrate, potassium bicarbonate, monopotassium phosphate, magnesium nitrate, magnesium sulfate, potassium sulfate, potassium chloride, sodium nitrates, magnesian limestone, magnesia, disodium dihydromolybdate, cobalt chlorid hexahydrate, nickel chloride hexahydrate, indole butyric acid, L-tryptophan, urea, urea-formaldehydes, urea ammonium nitrate, sulfur-coated urea, polymer-coated urea, isobutylidene diurea, K2SO4-2MgSO4, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion or a combination thereof. The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate or a combination thereof. The insecticide can include an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof. The herbicide can comprise a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carmabate, carbanilate, chloropyridinyl, a cyclohexenone derivative, a dinitroaminobenzene derivative, a fluorodinitrotoluidine compound, isoxazolidinone, nicotinic acide, isopropylamine, an isopropulamine derivative, oxadiazolinone, a phosphate, a phthalate, a picolinic acid compound, a triazine, a triazole, a uracil, a urea derivative, endothall, sodium chlorate, or a combination thereof. The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof. The fungal inoculant can comprise a fungal inoculant of the family Glomeraceae, a fungal inoculant of the family Claroidoglomeraceae, a fungal inoculant of the family Acaulosporaceae, a fungal inoculant of the family Sacculospraceae, a fungal inoculant of the family Entrophosporaceae, a fungal inoculant of the family Pacidsproraceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporacea, a fungal inoculant of the family Scutellosproaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, a fungal inoculant of the genus *Glomus*, or a combination thereof. The bacterial inoculant can include a bacterial inoculant of the genus *Rhizobium*, bacterial inoculant of the genus *Bradyrhizobium*, bacterial inoculant of the genus *Mesorhizobium*, bacterial inoculant of the genus *Azorhizobium*, bacterial inoculant of the genus *Allorhizobium*, bacterial inoculant of the genus *Sinorhizobium*, bacterial inoculant of the genus *Kluyvera*, bacterial inoculant of the genus *Azotobacter*, bacterial inoculant of the genus *Burkholderia*, bacterial inoculant of the genus *Pseudomonas*, bacterial inoculant of the genus *Azosprillium*, bacterial inoculant of the genus *Bacillus*, bacterial inoculant of the genus *Streptomyces*, bacterial inoculant of the genus *Paenibacillus*, bacterial inoculant of the genus *Paracoccus*, bacterial inoculant of the genus *Enterobacter*, bacterial inoculant of the genus *Alcaligenes*, bacterial inoculant of the genus *Mycobacterium*, bacterial inoculant of the genus *Trichoderma*, bacterial inoculant of the genus *Gliocladium*, bacterial inoculant of the genus *Klebsiella*, or a combination thereof.

For the purpose of the current invention, an "agriculturally compatible carrier" may be a natural or synthetic, organic or inorganic material with which the active compounds (e.g. the *A. oxydans* strain of the current application or one or more products derived from a culture of said *A. oxydans* strain) are combined to facilitate their application into the plant or to the plant growth medium.

Said "agriculturally compatible carrier" which can be regarded as a vehicle, is generally inert and it must be acceptable in agriculture. Thus, the phrase "agriculturally compatible" denotes a substance that can be used routinely under field conditions without interfering with growers' planting equipment, and without adversely influencing crop development or the desired ecological balance in a cultivated area.

The agriculturally compatible carrier can be solid. Solid carriers can include but are not limited to clays, natural or synthetic silicates, silica, resins, waxes, solid fertilizers, a polymer, a granular mass, perlite, a perlite granule, peat, a peat pellet, soil, vermiculite, charcoal, sugar factory carbonation press mud, rice husk, carboxymethyl cellulose, fine sand, calcium carbonate, flour, alum, a starch, talc, polyvinyl pyrrolidone, or a combination thereof. The agriculturally compatible carrier can be a liquid. Liquid carriers can include but are not limited to water, alcohols, ketones, petroleum fractions, oils, aromatic or paraffinic hydrocarbons, chlorinated hydrocarbons, liquefied gases or a combination thereof. More particularly, the agriculturally compatible carrier can include a dispersant, a surfactant, an additive, a thickener, an anti-caking agent, residue breakdown, a composting formulation, a granular application, diatomaceous earth, a coloring agent, a stabilizer, a preservative, a polymer, a coating or a combination thereof. One of the ordinary skills in the art can readily determine the appropriate carrier to be used taking into consideration factors such as a particular bacterial strain, plant to which the inoculum is to be applied, type of soil, climate conditions, whether the inoculum is in liquid, solid or powder form, and the like. The additive can comprise an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutant dioate, a benzene acetonitrile derivative, a proteinaceous material, or a combination thereof. The proteinaceous material can include a milk product, wheat flour, soybean meal, blood, albumin, gelatin, or a combination thereof. The thickener can comprise a long chain alkylsulfonate of polyethylene glycol, polyoxyethylene oleate or a combination thereof. The surfactant can contain a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof. The anti-caking agent can include a sodium salt such as a sodium sulfite, a sodium sulfate, a sodium salt of monomethyl naphthalene sulfonate, or a combination thereof; or a calcium salt such as calcium carbonate, diatomaceous earth, or a combination thereof. The agriculturally compatible carrier can also include a fertilizer, a micronutrient fertilizer material, an insecticide, a herbicide, a plant growth amendment, a fungicide, a molluscicide, an algicide, a bacterial inoculant, a fungal inoculant, or a combination thereof. Non-limiting examples are provided above.

As way of example, the strains of the current application or the supernatant of its culture or an extract of its culture may be mixed with an agriculturally compatible carrier. In some embodiments, the strains may be lyophilized or freeze-dried to a powder or aqueous slurry of said strain or combinations thereof according to the current invention may be dried to a powder at a temperature which does not adversely affect viability of the micro-organism. The powder may then be mixed with an agriculturally compatible carrier. In other embodiments, a liquid suspension of one or more strains of the current invention or the supernatant of a culture of said strains may be applied to an absorbent material, e.g. a granular mass, or may be used to coat plant seeds or other plant tissues.

A "plant propagule" is any plant material for the purpose of plant propagation. Because of the totipotency of plants, any part of the plant may be used (e.g. a stem cutting, a leaf section, a portion of a root), though it is usually a highly meristematic part such as root and stem ends, buds, tubers, bulbs, rhizome, stolon or any plant part for vegetative reproduction. In sexual reproduction, a propagule is a seed or spore.

A "plant seed coated" or alternatively a "coated seed" as used in this application refers to a plant seed covered with a certain composition. This composition (i.e. the coating composition) can be a water composition or an oil composition or a polymer. "Coating" includes the most simple covering methods of dipping seeds or plant propagules in a microbial suspension or spraying seeds or propagules with a microbial suspension. In the latter case, the coating compositions are found to be film-forming, i.e., upon contacting with seeds or propagules they form a thin liquid film that adheres to the surface. "Coating" also includes rolling seeds/propagules in or dusting seeds/propagules with or brushing seeds/propagules with a powder comprising microorganisms, to more complex procedures as injecting plant seeds/propagules with a composition comprising microorganism or the use of complex coating layers including one or more adhesive, binder solvent and/or filler components. A person skilled in the art is familiar with a variety of conventional and more advanced methods to coat plants seeds (e.g. U.S. Pat. No. 5,113,619, EP0080999, WO1997036471, EP0010630, WO2006131213, WO2001045489, U.S. Pat. No. 4,465,017, EP2676536 which are here all incorporated as reference). The coating composition can include a number of ingredients, including but not limited to gelatin, a desiccant, water, tallow (e.g. to increase the release rate of any active ingredient in the composition), bulking agents (e.g. clay, and bentonite to give more body to the liquid coating composition). Coating compositions which include bulking agents produce more rounded coated seeds. Such coated seeds are generally easier to plant when using mechanical planters. The concentration of the bulking agent can be up to about 50 percent of the solids by volume. As way of example of a liquid coating procedure, seeds or propagules are fed into one or more tanks containing the liquid coating composition. The seeds or propagules are transported from the tanks into a drying zone where forced air dries and solidifies the coating applied to the seeds. The seeds or propagules are dipped at least once and preferably at least twice in the liquid coating composition of the present invention. The dried coated seeds or propagules can be sowed or planted using standard sowing or planting machinery or by hand. In the alternative, the coated seeds or propagules can be stored for later application. If the temperature and humidity are relatively high or if prolonged storage is contemplated, it is desirable to place on the surface of the coating an inert material, preferably a powder material, such as, chalk or talcum powder. Such inert material reduces the tendency for the seed to stick together or agglomerate. The coating should cover more than 50%, more than 60%, more than 70%, more than 80%, more than 90, more than 95% of the surface area of the seeds or propagules. In some embodiments, after the coating procedure, the seeds should comprise at least one living cell of the isolated A. oxydans strain deposited as LMG P-29827. In other embodiments, after the coating procedure, the seeds should comprise at least an effective amount of one or more extracts of a culture of the isolated A. oxydans strain deposited as LMG P-29827. The coating layer can also consist of one or more components. These components can be additional plant growth promoting microorganisms but can also be fertilizers, biocontrol agents, or pesticides including fungicides, insecticides and herbicides. Non-limiting examples of these components are provided above. The coating composition can also include protective colloids, adhesives, thickening agents, thixotropic agents, penetrating agents, stabilizing agents, sequestering agents, fertilizers, anti-freeze agents, repellents, color additives, corrosion inhibitors, water-repelling agents, siccatives, UV-stabilizers, pigments, dyes or polymers. "Population" as used in this application refers to a group or collection of organisms. These organisms can but don't have to be part of the same species and do not need to originate from the same geographical area and do not need to have the capability of interbreeding. "Microbial" as used herein refers to microorganisms, wherein said microorganisms can include bacteria, archaebacteria, fungi, yeasts, mycorrhiza, microscopic eukaryotes (e.g. protozoa and algae), viruses, viroids or a combination thereof. A "microbial population" as used herein can thus refer to a synthetic or artificial collection of different microorganisms with distinct geographical origins. In various more particular embodiments of this application, "microbial" refers to "bacterial".

The term "artificial" is synonym for "synthetic" or "non-natural" and refers to a man-made condition, meaning that a natural occurring bacterial culture comprising one or more strains according to the current invention does not fall within the scope of this application. Already the term "bacterial culture" as defined above is limiting and is excluding natural occurring populations since bacteria in natural conditions will always grow in the presence of non-bacterial microorganisms.

The term "inoculating" as used herein refers to introducing at least one bacterium into a plant growth medium. By way of example and without the intention to be limiting, said introduction can be performed using a liquid, a powder, a granule, a pellet. "Plant growth medium" is defined as any environment wherein plants can grow. Non-limiting examples of a plant growth medium are soil, sand, gravel, a polysaccharide, mulch, compost, peat moss, straw, logs, clay, or a combination thereof. A plant growth medium can also include a hydroculture system or an in vitro culture system. Hydroculture is the growing of plants in a soilless medium or an aquatic based environment, while in vitro culture system refers to the growing of plants or explants on or in a recipient with synthetic medium, in sterile conditions, in a controlled environment and in reduced space. Explants refer to parts of a plant, from all the aerial part to isolated cells, as parts of leaves, of roots, seeds, bulbs, tubers, buds. The inoculation of said plant growth medium with a microbial population can be done before, during and/or after sowing or before, during and/or after the start of the plant growth cycle in case of hydroculture or in vitro culture. The inoculation can be performed once or multiple times during the plant growth cycle.

"Nutrient" or "nutrients" as used herein refers to chemical elements and compounds necessary for plant growth and plant metabolism. Some essential plant nutrients include carbon and oxygen which are absorbed by the plant from the air, while other nutrients including water are typically obtained from the growing medium. "Nutrients" include both macronutrients and micronutrients. Macronutrients are generally required in large quantities and are usually present in plant tissue in concentrations of between 0.2% and 4% on a dry weight basis. Macronutrients are the building blocks of crucial cellular components like proteins and nucleic acids. Non-limiting examples of macronutrients are nitrogen, phosphorus, potassium, calcium, sulfur, magnesium. Carbon, hydrogen, and oxygen are also considered macronutrients as they are required in large quantities to build the larger organic molecules of the cell; however, they represent the non-mineral class of macronutrients. Micronutrients are required in very small amounts and are generally present in plant tissue in quantities less than 0.02% dry weight. Micronutrients are often required as cofactors for enzyme activity. Non-limiting examples of micronutrients are boron, chlorine, manganese, iron, zinc, copper, molybdenum, nickel. Mineral nutrients are usually obtained from the growing medium (e.g. soil) through plant roots, and many factors can affect the efficiency of nutrient uptake. First, the chemistry and composition of certain soils can make it harder for plants to absorb nutrients. The nutrients may not be available in certain soils, or may be present in forms that the plants cannot use. Soil properties like water content, pH, and compaction may exacerbate these problems. Administration of specific plant growth promoting microorganisms to the soil or to the plant can counter some uptake limiting conditions and increase the plant's nutrient uptake. As non-liming examples of how plant growth promoting microorganisms may play a role in modifying nutrient uptake and/or the nutrient use efficiency in soils is increasing phosphate solubility from either organic or inorganic bound phosphates, thereby facilitating plant growth or solubilizing iron in the soil by the secretion of siderophores, small high-affinity iron chelating compounds. In more particular embodiments, a microbial population comprising an isolated *A. oxydans* strain is provided to increase nutrient uptake and/or nutrient use efficiency of a plant, wherein said nutrient is selected from nitrogen, potassium, and phosphorus.

"Nutrient use efficiency" as used herein refers to the efficiency of a plant to take up a nutrient from the soil, but also on transport, storage, mobilization, usage of that nutrient within the plant. Nutrient use efficiency is defined as yield per unit input, wherein the input is typically macro- or micronutrients. Improvement of nutrient use efficiency is an essential pre-requisite for expansion of crop production into marginal lands with low nutrient availability or to maintain plant yield under reduced fertilization conditions.

In the art, the term "biofertilizer" is generally used to refer to a microbial fertilizer that supplies the plant with nutrients and thereby can promote plant growth in the absence of pathogen pressure.

For the purpose of the current invention, the term "nitrogen fixation" describes the process that causes free nitrogen to combine chemically with other elements to form more reactive nitrogen compounds such as ammonia, nitrates or nitrites. This can be done industrially but also naturally. In the latter case, nitrogen fixation is performed by nitrogen-fixing bacteria. Some of them are 'free-living', while others have entered into a symbiotic relationship with certain plants. In exchange for sugars and other nutrients supplied by the host plant, symbiotic nitrogen-fixing bacteria convert atmospheric nitrogen into ammonium (a form usable by the host plant) and pass it to the plant. The nitrogen fixating capacities of a plant depend on a plethora of biochemical processes. The term "culture" as used herein refers to a population of microorganisms that are propagated on or in media of various kinds. An "enriched culture" of the above described strains refer to a culture of microorganisms wherein the total microbial population of the culture contains more than 50%, more than 60%, more than 70%, more than 80%, more than 90%, or more than 95% of the isolated strains of the current invention. This is equivalent as saying that a culture of microorganisms is provided, wherein said culture is enriched with the above described strains and wherein "enriched" means that the total microbial population of said culture contains more than 50%, more than 60%, more than 70%, more than 80%, more than 90%, or more than 95% of the isolated strains of the current application.

"Supernatant" refers to the liquid broth remaining when cells grown in broth are removed by centrifugation, filtration, sedimentation or other means well known in the art.

An "extract" as used herein refers to various forms of microbial products. These products are obtained by removing the cell walls and/or cell membranes of the microorganisms, a process also known as lysis, thereby obtaining one or more endogenous products of the cultured microorganisms. Non-limiting examples of such products are amino acids, peptides, enzymes, secondary metabolites, vitamins, minerals. Removing the cell walls and/or cell membranes of the cultured microorganisms can be obtained by several procedures which are well-known by the person skilled in the art. Non-limiting examples are addition of chemicals (e.g. sodium chloride) to a microbial culture, heating the microbial culture or induce lysis in a mechanical way. An extract can also be obtained by autolysis of the microorganisms.

The term "free of disease and/or pathogen pressure and/or pest organisms" as used herein refers to a situation that does not significantly inhibit plant growth and/or yield. "Significantly inhibiting" as used herein means a reduction of plant growth and/or plant yield of at least 50%, at least 20%, at least 10% or at least 5% compared to a control plant that is not affected by disease and/or pathogen pressure and/or pest organisms.

"Phytopathogenic organisms" as used herein refer to organisms that cause plant disease and include fungi, oomycetes, bacteria, viruses, virus-like organisms, phytoplasmas, protozoa, nematodes and parasitic plants. "Pest organisms" as used herein are organisms that negatively affect plant health by e.g. consumption of plant tissue. Non-limiting examples of pest organisms are insects, mites, gastropods, vertebrates.

A "sprayable formulation" as used herein is an agrochemical or a biological solution that can be sprinkled on a plant or soil. The formulation is composed in such a way that the active ingredients can be absorbed by the above-ground tissue of a plant or is available for the plant roots when administered to the soil. The above disclosed methods thus also includes irrigation with a liquid comprising one or more strains of the current invention.

"Irrigating" or "irrigation" as used herein refers to the method in which water or other liquids are supplied to plants at regular intervals. Irrigation includes but is not limited to "localized irrigation" (i.e. a system where water is distributed under pressure through a piped network, in a predetermined pattern, and applied as a small discharge to each plant or adjacent to it. "Drip (or micro) irrigation", also known as "trickle irrigation" (i.e. a system where water falls drop by drop just at the position of roots or near the root zone of plants) and "sprinkler irrigation" (i.e. a system where water is distributed by overhead sprinklers) belong to this category of irrigation methods. In "sprinkler irrigation", sprinklers can also be mounted on moving platforms connected to the water source by a hose. Automatically moving wheeled systems known as traveling sprinklers may irrigate areas such as small farms, sports fields, parks, pastures, and cemeteries unattended. Most of these utilize a length of polyethylene tubing wound on a steel drum. As the tubing is wound on the drum powered by the irrigation water or a small gas engine, the sprinkler is pulled across the field. When the sprinkler arrives back at the reel the system shuts off. This type of system is known to most people as a "waterreel" traveling irrigation sprinkler.

Invention

The current invention pertains to the use of isolated bacterial strains or combinations thereof for enhancing plant growth and development.

Therefore in a first aspect, an enriched bacterial culture comprising at least one isolated *Streptomyces* strain and at least one isolated *Arthrobacter* strain is provided.

The inventors of the current invention found that such cultures are particularly useful for enhancing plant growth.

By preference, said isolated *Streptomyces* strain is chosen from the group of *Streptomyces griseus, Streptomyces olivoviridis, Streptomyces cirratus, Streptomyces candidus, Streptomyces chryseus, Streptomyces peucetius, Streptomyces flaveus, Streptomyces griseoruber, Streptomyces bottropensis, Streptomyces phaeochromogenes, Streptomyces fradeiae, Streptomyces durmitorensis, Streptomyces coeruleofuscus, Streptomyces marokkonensis, Streptomyces althioticus, Streptomyces pseudogriseolus, Streptomyces azureus, Streptomyces niveus, Streptomyces afghaniensis, Streptomyces afghaniensis, Streptomyces ambofaciens Streptomyces argenteolus, Streptomyces bacillaris, Streptomyces armeniacus, Streptomyces cacaoi* subsp. *Cacaoi, Streptomyces caeruleus, Streptomyces carpaticus, Streptomyces canus, Streptomyces chumphonensis, Streptomyces capoamus, Streptomyces finlayi, Streptomyces chrestomyceticus, Streptomyces glomeroaurantiacus, Streptomyces cinereoruber, Streptomyces harbinensis, Streptomyces coelescens, Streptomyces olivaceus, Streptomyces cyanogenus, Streptomyces prasinopilosus, Streptomyces flavomacrosporus, Streptomyces specialis, Streptomyces floridae, Streptomyces umbrinus, Streptomyces galbus, Streptomyces xantholiticus, Streptomyces griseoruber, Streptomyces anthocyanicus, Streptomyces griseus, Streptomyces cavourensis, Streptomyces hygroscopicus, Streptomyces candidus, Streptomyces javensis, Streptomyces colombiensis, Streptomyces microflavus, Streptomyces galbus, Streptomyces pseudovenezuelae, Streptomyces griseoviridis, Streptomyces purpurogeneiscleroticus, Streptomyces griseoluteus, Streptomyces sahachiroi, Streptomyces spiroverticillatus, Streptomyces lavengulata, Streptomyces turgidiscabies Streptomyces lydicus, Streptomyces viridogenes, Streptomyces prasinus Streptomyces rimosus Streptomyces saraceticus.*

By preference, said isolated *Streptomyces* strain is a *Streptomyces* strain which comprises a 16S rRNA sequence exhibiting at least 97% sequence identity to SEQ ID N° 1. In another embodiment, an enriched bacterial culture is provided wherein said culture comprises the isolated *Streptomyces niveus* strain deposited as LMG P-29828.

Said isolated *Arthrobacter* strain is preferably chosen from the group of *Arthrobacter agilis, Arthrobacter pascens, Arthrobacter ramosus, Arthrobacter oryzae, Arthrobacter humicola, Arthrobacter oxydans, Arthrobacter globiformis, Citricoccus alkalitolerans, Arthrobacter aurescens, Arthrobacter tumbae, Arthrobacter arilaitensis, Arthrobacter crystallopoeietes, Kocuria rosea, Arthrobacter citreus, Arthrobacter subterraneus, Arthrobacter koreensis,*

By preference, said isolated *Arthrobacter* strain is an *Arthrobacter* strain which comprises a 16S rRNA sequence exhibiting at least 97% sequence identity to SEQ ID N° 2 or 3. In another embodiment, an enriched bacterial culture is provided wherein said culture comprises the isolated *Streptomyces niveus* strain deposited as LMG P-29827 or which can be obtained from the Microbial Strain Collection of Fundacion MEDINA in Spain with accession number CB-283399 CAJA 1-24. More preferably, said *Arthorbacter* strain is *Arthrobacter agilis* or *Arthrobacter oxydans*.

The strains of the bacterial culture of the current application are purified at least 2×, at least 5×, at least 10×, at least 50× or at least 100× from the raw material from which they are isolated. As a non-limiting example, if a microorganism is isolated from soil as raw material, the microorganism can be isolated to an extent that its concentration in a given quantity of purified or partially purified material (e.g. soil) is at least 2×, at least 5×, at least 10×, at least 50× or at least 100× that in the original raw material.

Thus, in one embodiment an artificial bacterial culture is provided wherein said culture comprises at least one isolated *Streptomyces* strain, whereby said *Streptomyces* strain may be an isolated *Streptomyces niveus* strain and at least one isolated *Arthrobacter* strain, whereby said strain may be an isolated *Arthrobacter oxydans* and/or *Arthrobacter agilis* strain.

In one embodiment, an enriched bacterial culture is provided wherein said culture comprises at least an isolated *Streptomyces niveus* strain and at least an isolated *Arthrobacter oxydans* and/or *Arthrobacter agilis* strain, wherein said *S. niveus* strain comprises a 16S rRNA sequence exhibiting at least 97% sequence identity to SEQ ID N° 1, wherein said *A. oxydans* strain comprises a 16S rRNA sequence exhibiting at least 97% sequence identity to SEQ ID N° 2 and wherein said *A. agilis* comprises a 16S rRNA sequence exhibiting at least 97% sequence identity to SEQ ID N° 3. In another embodiment, an enriched bacterial culture is provided wherein said culture comprises at least the isolated *Streptomyces niveus* strain deposited as LMG P-29828 and at least the isolated *Arthrobacter oxydans* strain deposited as LMG P-29827 and/or *A. agilis* obtainable from the Microbial Strain Collection of Fundacion MEDINA in Spain with accession number CB-283399 CAJA 1-24.

In another embodiment, a supernatant is provided wherein said supernatant is obtained from the bacterial culture of the current application. In a more particular embodiment, a supernatant is provided wherein said supernatant is obtained from an enriched bacterial culture comprising an isolated *Streptomyces* strain, preferably *Streptomyces niveus* and an isolated *Arthrobacter* strain, preferably *Arthrobacter oxydans* or *agilis*. Said *S. niveus* strain comprises a 16S rRNA sequence exhibiting at least 97% sequence identity to SEQ ID N° 1 and wherein said *A. oxydans* strain comprises a 16S rRNA sequence exhibiting at least 97% sequence identity to SEQ ID N° 2. Said *A. agilis* strain comprises an rRNA sequence exhibiting at least 97% sequence identity to SEQ ID N° 3. In an even more particular embodiment, a supernatant is provided wherein said supernatant is obtained from an enriched bacterial culture comprising an isolated *Streptomyces niveus* strain deposited as LMG P-29828 and an isolated *Arthrobacter oxydans* strain deposited as LMG P-29827 and/or an isolated *Arthrobacter agilis* strain available under accession number CB-283399 CAJA 1-24.

In another embodiment, an extract is provided wherein said extract is obtained from the bacterial culture of the current application. In a more particular embodiment, an extract is provided wherein said extract is obtained from an enriched bacterial culture comprising an isolated *Streptomyces* strain, preferably a *Streptomyces niveus* strain and an isolated *Arthrobacter* strain, preferably an *Arthrobacter oxydans* or *agilis* strain. Said *S. niveus* strain comprises a 16S rRNA sequence exhibiting at least 97% sequence identity to SEQ ID N° 1 and wherein said *A. oxydans* strain comprises a 16S rRNA sequence exhibiting at least 97% sequence identity to SEQ ID N° 2. In an even more particular embodiment, an extract is provided wherein said extract is obtained from an enriched bacterial culture comprising an isolated *Streptomyces niveus* strain deposited as LMG P-29828 and an isolated *Arthrobacter oxydans* strain deposited as LMG P-29827. Said *A. agilis* strain comprises an rRNA sequence exhibiting at least 97% sequence identity to SEQ ID N° 3.

In another embodiment, a composition comprising the bacterial culture of the current application or an enriched bacterial culture comprising an isolated *Streptomyces niveus* strain and an isolated *Arthrobacter oxydans* or *agilis* strain, wherein said *S. niveus* strain comprises a 16S rRNA sequence exhibiting at least 97% sequence identity to SEQ ID N° 1 and wherein said *A. oxydans* strain comprises a 16S rRNA sequence exhibiting at least 97% sequence identity to SEQ ID N° 2 and *A. agilis* strain comprises an rRNA sequence exhibiting at least 97% sequence identity to SEQ ID N° 3. Alternatively, the enriched bacterial culture may comprise the isolated *Streptomyces niveus* strain deposited as LMG P-29828 and the isolated *Arthrobacter oxydans* strain deposited as LMG P-29827 and/or the *A. agilis* strain obtainable via accession number CB-283399 CAJA 1-24. Also a composition is provided wherein said composition comprises one or more products derived from the bacterial culture of the current invention or one of the other above mentioned enriched bacterial cultures. Said one or more products can be obtained from the supernatant or from an extract of said culture Also, the current invention provides a composition comprising an isolated *Streptomyces* strain, preferably *Streptomyces niveus* as described above and an isolated *Arthrobacter* strain, preferably an *Arthrobacter oxydans* and/or *agilis* and at least one microorganism selected from the list consisting of *Bacillus subtilis* strain 713, *Bacillus amyloliquefaciens* MBI 600, *Bacillus pumillus* QST2808, *Pseudomonas fluorescens*, *Bradyrhizobium japonicum*, *Trichoderma vireus*, *Pseudomonas putida*, *Trichoderma harzianum Rifai* strain T22, *Penicillium bilaii*, *Mesorhizobium*, *Azospirillum*, *Azotobacter vinelandii* and *Clostridium pasteurianum*.

In another embodiment, a combination comprising the bacterial culture of the current application or one of the other above mentioned enriched bacterial cultures and an agriculturally compatible carrier is provided. Also a combination is provided comprising an agriculturally compatible carrier and one or more products derived from the bacterial culture of the current application or of one of the other above mentioned enriched bacterial cultures.

As way of example, the bacterial culture of the current invention or the supernatant of said culture or an extract of said culture may be mixed with an agriculturally compatible carrier. In some embodiments, the bacterial culture of the current application or one of the other above mentioned enriched bacterial cultures may be lyophilized or freeze-dried to a powder or an aqueous slurry of the bacterial culture of the current application or one of the other above mentioned enriched bacterial cultures may be dried to a powder at a temperature which does not adversely affect viability of the micro-organisms. The powder may then be mixed with an agriculturally compatible carrier. In other embodiments, a liquid suspension of the bacterial culture of the current application or of one of the other above mentioned enriched bacterial cultures or the supernatant of one of said cultures may be applied to an absorbent material, e.g. a granular mass, or may be used to coat plant seeds or other plant tissues.

Thus in another embodiment, a plant seed or plant propagule coated with the bacterial culture of the current application is provided. This is equivalent as saying that a plant seed or plant propagule is provided, wherein said plant seed or propagule having applied to the surface of said seed or of said propagule, an enriched bacterial culture comprising at least an isolated *Streptomyces* strain, preferably *S. niveus* strain and an isolated *Arthrobacter* strain, preferably an *A. oxydans* and/or *A. agilis* strain. In another embodiment, a plant seed or plant propagule is provided wherein said seed or said propagule is coated with an enriched bacterial culture comprising an isolated *Streptomyces niveus* strain and an isolated *Arthrobacter oxydans* and/or *Arthrobacter agilis* strain, wherein said *S. niveus* strain comprises a 16S rRNA sequence exhibiting at least 97% sequence identity to SEQ ID N° 1, wherein said *A. oxydans* strain comprises a 16S rRNA sequence exhibiting at least 97% sequence identity to SEQ ID N° 2 and wherein said *A. agilis* strain comprises an rRNA sequence exhibiting at least 97% sequence identity to SEQ ID N° 3. This is equivalent as saying that a plant seed or plant propagule is provided, said plant seed or propagule having applied to the surface of said seed or of said propagule at least an isolated *S. niveus* strain comprising a 16S rRNA sequence exhibiting at least 97% sequence identity to SEQ ID N° 1 and an isolated *A. oxydans* strain comprises a 16S rRNA sequence exhibiting at least 97% sequence identity to SEQ ID N° 2 and/or an *A. agilis* strain comprises an rRNA sequence exhibiting at least 97% sequence identity to SEQ ID N° 3. In another embodiment, a plant seed or plant propagule is provided wherein said seed or said propagule is coated with an enriched bacterial culture comprising the isolated *Streptomyces niveus* strain deposited as LMG P-29828 and the isolated *Arthrobacter oxydans* strain deposited as LMG P-29827 and/or the *A. agilis* strain obtainable via accession number CB-283399 CAJA 1-24. This is equivalent as saying that a plant seed or plant propagule is provided, said plant seed or propagule having applied to the surface of said seed or of said propagule at least the isolated *Streptomyces niveus* strain deposited as LMG P-29828 and the isolated *Arthrobacter oxydans* strain deposited as LMG P-29827 and/or the *A. agilis* strain obtainable via accession number CB-283399 CAJA 1-24.

In some embodiments, after the coating procedure, the seeds should comprise at least one living cell of the *Streptomyces niveus* strain of the bacterial culture of the application and at least one living cell of the *Arthrobacter oxydans* and/or *agilis* strain of the bacterial culture of the invention. In other embodiments, after the coating procedure, the seeds should comprise at least an effective amount of one or more extracts of the bacterial culture of the current application or of one of the other above mentioned bacterial cultures. The coating layer can also consist of one or more components. These components can be additional plant growth promoting microorganisms but can also be fertilizers, biocontrol agents, or pesticides including fungicides, insecticides and herbicides. Non-limiting examples of these components are provided above. The coating composition can also include protective colloids, adhesives, thickening agents, thixotropic agents, penetrating agents, stabilizing agents, sequestering agents, fertilizers, anti-freeze agents, repellents, color additives, corrosion inhibitors, water-repelling agents, siccatives, UV-stabilizers, pigments, dyes or polymers.

In alternative versions of the first aspect and of all its accompanying above described embodiments, the *S. niveus* strain of said bacterial culture is an isolated *S. niveus* strain comprising a 16S rRNA sequence exhibiting at least 98% sequence identity to SEQ ID N° 1 whereas the *A. oxydans* strain of said bacterial culture is an isolated *A. oxydans* strain comprising a 16S rRNA sequence exhibiting at least 98% sequence identity to SEQ ID N° 2 and the *A. agilis* strain comprises an rRNA sequence exhibiting at least 98% sequence identity to SEQ ID N° 3. In other alternative versions of the first aspect and of all its accompanying above described embodiments, the *S. niveus* strain of said bacterial culture is an isolated *S. niveus* strain comprising a 16S rRNA sequence exhibiting at least 99% sequence identity to SEQ ID N° 1 and the *A. oxydans* strain of said bacterial culture is an isolated *A. oxydans* strain comprising a 16S rRNA sequence exhibiting at least 99% sequence identity to SEQ ID N° 2 *A. agilis* strain comprises an rRNA sequence exhibiting at least 99% sequence identity to SEQ ID N° 3. In other alternative versions of the first aspect and of all its accompanying above described embodiments, the *S. niveus* strain of said bacterial culture is an isolated *S. niveus* strain comprising a 16S rRNA sequence exhibiting at least 100% sequence identity to SEQ ID N° 1 and the *A. oxydans* strain of said bacterial culture is an isolated *A. oxydans* strain comprising a 16S rRNA sequence exhibiting at least 100% sequence identity to SEQ ID N° 2 *A. agilis* strain comprises an rRNA sequence exhibiting at least 100% sequence identity to SEQ ID N° 3. In other alternative versions of the first aspect and of all its accompanying above described embodiments, the *S. niveus* strain of said bacterial culture is the isolated *S. niveus* strain deposited as LMG P-29828 and the *A. oxydans* strain of said bacterial culture is the isolated *Arthrobacter oxydans* strain deposited as LMG P-29827, whereas the *A. agilis* strain obtainable via accession number CB-283399 CAJA 1-24.

The enriched bacterial culture as described above in all its embodiments may be used for various purposes, such as enhancing plant yield and/or plant growth, increase of nutrient uptake and/or nutrient use efficiency of a plant, increase of nitrogen fixating capacities of a plant. These aspects will be described more in detail below.

In a second aspect, an enriched bacterial culture comprising an isolated *Streptomyces* strain as described above, preferably a *S. niveus* strain and an isolated *Arthrobacter* strain as described above, preferably an *A. oxydans* and/or *A. agilis* strain is provided to enhance plant yield and/or plant growth. This is equivalent as saying that an enriched bacterial culture comprising an isolated *Streptomyces* strain such as *S. niveus* strain and at least one isolated *Arthrobacter* strain such as an *A. oxydans* or *agilis* strain has plant growth promoting activity, as demonstrated in the Examples.

In particular embodiments, said *S. niveus* strain of said bacterial culture provided to enhance plant yield and/or plant growth is an isolated *S. niveus* strain comprising a 16S rRNA sequence exhibiting at least 97% sequence identity, more preferably 98% sequence identity, even more preferably 99% sequence identity or 100% sequence identity to SEQ ID N° 1. Said *A. oxydans* strain of said bacterial culture is an isolated *A. oxydans* strain comprising a 16S rRNA sequence exhibiting at least 97% sequence identity, more preferably 98% sequence identity, even more preferably 99% sequence identity or 100% sequence identity to SEQ ID N° 2.

Said *A. agilis* strain preferably comprises a 16S rRNA sequence exhibiting at least 97% sequence identity, more preferably 98% sequence identity, even more preferably 99% sequence identity or 100% sequence identity to SEQ ID N° 3.

In other particular embodiments, said *S. niveus* strain of said bacterial culture provided to enhance plant yield and/or plant growth is the isolated *S. niveus* strain deposited as LMG P-29828 whereas said *A. oxydans* strain of said bacterial culture is the isolated *Arthrobacter oxydans* strain deposited as LMG P-29827 the *A. agilis* strain obtainable via accession number CB-283399 CAJA 1-24.

Thus, as non-limiting examples, the bacterial population comprising an isolated *Streptomyces* strain such as *S. niveus* strain and an isolated *Arthrobacter* strain such as an *A. oxydans* and/or *agilis* strain may produce an above stated percentage increase in nitrogen fixation, or an above stated increase in total root weight, or in leaf area or in plant product yield (e.g. an above stated percentage increase in plant product weight), or an increased accumulated biomass of the plant.

Thus in a more particular embodiment, an enriched bacterial population comprising an isolated *S. niveus* strain and an isolated *A. oxydans* strain is provided to enhance plant yield, more particularly an enriched bacterial culture comprising an isolated *S. niveus* strain comprising a 16S rRNA sequence exhibiting at least 97% sequence identity, more preferably 98% sequence identity, even more preferably 99% sequence identity or 100% sequence identity to SEQ ID N° 1 and an isolated *A. oxydans* strain comprising a 16S rRNA sequence exhibiting at least 97% sequence identity, more preferably 98% sequence identity, even more preferably 99% sequence identity or 100% sequence identity to SEQ ID N° 2 is provided to enhance plant yield. Said *A. agilis* strain preferably comprises a 16S rRNA sequence exhibiting at least 97% sequence identity, more preferably 98% sequence identity, even more preferably 99% sequence identity or 100% sequence identity to SEQ ID N° 3.

In another embodiment an enriched bacterial population comprising the isolated *S. niveus* strain deposited as LMG P-29828 and the isolated *A. oxydans* strain deposited as LMG P-29827 and/or an *A. agilis* strain obtainable via accession number CB-283399 CAJA 1-24 is provided to enhance plant yield.

In a more particular embodiment, said enriched bacterial culture as described above is provided to enhance plant yield and/or plant growth in the absence of plant disease, of pathogen pressure or phytopathogenic organisms and/or pest organisms. Signs and symptoms of plant disease can be evaluated and interpreted by a person skilled in the art of plant pathology. Practitioners are particularly directed to Westcott's Plant Disease Handbook. Non-limiting examples of plant disease symptoms and signs are spots on leaves or on fruit, aberrant coloring of leaves, rot of leaves or fruit or roots, shoot or leaf blight, wilting, and presence of gals or tumors.

In an even more particular embodiment, the enriched bacterial culture according to the current invention is provided to enhance plant yield and/or plant growth in the absence of salt (NaCl) stress and/or drought stress.

In yet another embodiment, an enriched bacterial culture according to the current invention is provided to increase nutrient uptake and/or nutrient use efficiency of a plant.

In more particular embodiments, an enriched bacterial culture according to the current invention comprising an isolated *Streptomyces* such as *S. niveus* strain and an isolated *Arthrobacter* such as an *A. oxydans* and/or *agilis* strain is provided to increase nutrient uptake and/or nutrient use efficiency of a plant, wherein said nutrient is nitrogen, potassium, or phosphorus.

Second, to increase the efficiency of nutrient uptake, some plants possess mechanisms or structural features that provide advantages when growing in certain types of nutrient limited soils. One of the most universal adaptations to nutrient-limited soils is a change in root structure that may increase the overall surface area of the root to increase nutrient uptake or may increase elongation of the root system to access new nutrient sources. Administration of PGP bacteria can positively affect the root system (as demonstrated in this application) leading to an increase in the uptake of resources and a stimulation of overall plant growth. Thus in a particular embodiment, an enriched bacterial culture according to the current invention comprising an isolated *Streptomyces*, preferably a *S. niveus* strain and an isolated *Arthrobacter*, preferably an *A. oxydans* and/or *agilis* strain is provided to stimulate the growth of the plant's root system. In a more particular embodiment, said isolated *S. niveus* strain comprises a 16S rRNA sequence exhibiting at least 97%, more preferably 98% sequence identity, even more preferably 99% sequence identity or 100% sequence identity to SEQ ID N° 1 and said isolated *A. oxydans* strain comprises a 16S rRNA sequence exhibiting at least 97% sequence identity, more preferably 98% sequence identity, even more preferably 99% sequence identity or 100% sequence identity to SEQ ID N° 2. Said *A. agilis* strain preferably comprises a 16S rRNA sequence exhibiting at least 97% sequence identity, more preferably 98% sequence identity, even more preferably 99% sequence identity or 100% sequence identity to SEQ ID N° 3.

In another embodiment, said isolated *S. niveus* strain is deposited as LMG P-29828 and the isolated *A. oxydans* deposited is as LMG P-29827, whereas said *A. agilis* strain obtainable via accession number CB-283399 CAJA 1-24.

Supported by the experiments described in the Examples, the bacterial culture of the application is regarded a biofertilizer. Thus, in another embodiment, an enriched bacterial culture comprising an isolated *Streptomyces* strain as described above, preferably a *S. niveus* strain and at least one isolated *Arthrobacter* strain as described above, preferably an *A. oxydans* or *A. agilis* strain is provided for use as a biofertilizer, more particularly, said isolated *S. niveus* strain comprising a 16S rRNA sequence exhibiting at least 97%, more preferably 98%, even more preferably 99%, or 100% sequence identity to SEQ ID N° 1 and said isolated *A. oxydans* strain comprising a 16S rRNA sequence exhibiting at least 97% more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3. In yet another embodiment, an enriched bacterial culture comprising the isolated *S. niveus* strain deposited as LMG P-29828, the isolated *A. oxydans* deposited as LMG P-29827 and/or the isolated *A. agilis* accessible via CB-283399 CAJA 1-24 is provided for use as a biofertilizer.

In another embodiment, an enriched bacterial culture comprising at least a *Streptomyces* strain as described above, preferably an isolated *S. niveus* strain and at least one *Arthrobacter* strain as described above, preferably an isolated *A. oxydans* and/or *A. agilis* strain is provided to increase the nutrient uptake and/or nutrient use efficiency of a plant, wherein said plant is not a leguminous plant. As a more particular extension of the latter embodiment, said nutrient is selected from nitrogen, potassium and phosphorus. In an even more particular extension of the latter embodiment, said nutrient is nitrogen. In another embodiment, an enriched bacterial culture comprising an isolated *S. niveus* strain and an isolated *A. oxydans* or *agilis* strain is provided to increase the nutrient uptake and/or nutrient use efficiency of a plant, wherein said plant is not a leguminous plant and wherein said isolated *S. niveus* strain comprises a 16S rRNA sequence exhibiting at least 97% more preferably 98%, even more preferably 99%, or 100% sequence identity to SEQ ID N° 1 and wherein said isolated *A. oxydans* strain comprises a 16S rRNA sequence exhibiting at least 97% more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3. As a more particular extension of the latter embodiment, said nutrient is selected from nitrogen, potassium and phosphorus. In an even more particular extension of the latter embodiment, said nutrient is nitrogen. In another embodiment, an enriched bacterial culture comprising the isolated *S. niveus* strain deposited as LMG P-29828, the isolated *A. oxydans* strain deposited as LMG P-29827 and/or the isolated *A. agilis* accessible via CB-283399 CAJA 1-24 is provided to increase the nutrient uptake and/or nutrient use efficiency of a plant, wherein said plant is not a leguminous plant. As a more particular extension of the latter embodiment, said nutrient is selected from nitrogen, potassium and phosphorus. In an even more particular extension of the latter embodiment, said nutrient is nitrogen.

In another embodiment, an enriched bacterial culture comprising at least a *Streptomyces* strain as described above, preferably an isolated *S. niveus* strain and at least one *Arthrobacter* strain as described above, preferably an isolated *A. oxydans* or *agilis* strain is provided to increase the nitrogen fixating capacities of a plant. In a more particular embodiment, an enriched bacterial culture comprising an isolated *S. niveus* strain and an isolated *A. oxydans* strain is provided to increase the nitrogen fixating capacities of a plant wherein said isolated *S. niveus* strain comprises a 16S rRNA sequence exhibiting at least 97%, more preferably 98%, even more preferably 99%, or 100% sequence identity to SEQ ID N° 1 and wherein said isolated *A. oxydans* strain comprises a 16S rRNA sequence exhibiting at least 97%, more preferably 98%, even more preferably 99%, or 100% sequence identity to SEQ ID N° 2 whereas said *A. agilis* comprises a 16S rRNA sequence exhibiting at least 97% more preferably 98%, even more preferably 99%, or 100% sequence identity to SEQ ID N° 3. In a more particular embodiment, an enriched bacterial culture comprising the isolated *S. niveus* strain deposited as LMG P-29828, the isolated *A. oxydans* strain deposited as LMG P-29827 and/or the isolated *A. agilis* accessible via CB-283399 CAJA 1-24 is provided to increase the nitrogen fixating capacities of a plant.

Plant growth promoting microorganisms produce compounds which can be secreted in the bacterial medium or can be stored in the cells. Therefore, in alternative embodiments the use of a supernatant or of an extract of the bacterial culture as described above is provided to enhance plant growth and/or yield. In more particular embodiments, the use of a supernatant or of an extract of said bacterial culture of the latter embodiment is provided to enhance nutrient uptake and/or nutrient use efficiency of a plant. In even more particular embodiment, the use of a supernatant or of an extract of said bacterial culture is provided to increase the nitrogen fixating capacities of a plant.

In all above described embodiments of this second aspect, "enhance" or "increase" or "improvement" refers to an at least 5% increase or at least 10% increase or at least 25% increase or at least 50% increase or at least 75% increase or at least a 100% increase in the property being measured.

In a third aspect, a method is provided for enhancing plant growth and/or plant yield, said method comprising:
  inoculating a plant growth medium with an enriched bacterial culture of one of the embodiments as described above, wherein said culture comprises at least an isolated *Streptomyces* strain, preferably *S. niveus* strain and at least an isolated *Arthrobacter* strain, preferably an *A. oxydans* or *agilis* strain;
  growing a plant in said medium;
  to enhance growth and/or yield of said plant.

In one embodiment, said isolated *S. niveus* strain comprises a 16S rRNA sequence exhibiting at least 97%, more preferably 98%, even more preferably 99%, or 100% sequence identity to SEQ ID N° 1 and said isolated *A. oxydans* strain comprises a 16S rRNA sequence exhibiting at least 97%, more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3. In another embodiment, said isolated *S. niveus* strain is the *S. niveus* strain deposited as LMG P-29828, said isolated *A. oxydans* strain is the *A. oxydans* strain deposited as LMG P-29827 and the isolated *A. agilis* accessible via CB-283399 CAJA 1-24.

In a particular embodiment, a method is provided for enhancing growth and/or yield of a plant, wherein said plant is free of disease and/or pathogen pressure and/or pest organisms, said method comprising:
  inoculating a plant growth medium with an enriched bacterial culture as described above, wherein said culture comprises an isolated *Streptomyces* strain, preferably an *S. niveus* strain and an isolated *Arthrobacter* strain, preferably an *A. oxydans* or *agilis* strain;
  growing said plant in said medium;
  to enhance growth and/or yield of said plant.

In another embodiment, a method is provided for enhancing growth and/or yield of a plant, wherein said plant is grown in the absence of salt (NaCl) stress and wherein said method comprising:
  inoculating a plant growth medium with an enriched bacterial culture as described above, wherein said culture comprises an isolated *Streptomyces* strain, preferably an isolated *S. niveus* strain and an isolated *Arthrobacter* strain, preferably an *A. oxydans* or *agilis* strain;
  growing said plant in said medium;
  to enhance growth and/or yield of said plant in the absence of salt (NaCl) stress.

The inoculation can be performed once or multiple times during the plant growth cycle. The application also envisages the inoculation of the plant growth medium with the supernatant or with an extract of the bacterial culture as described above, comprising at least an isolated *Streptomyces* strain, preferably *S. niveus* strain and an at least an *Arthrobacter* strain, preferably an isolated *A. oxydans* or *agilis* strain. More particularly said enriched bacterial culture comprises an isolated *S. niveus* strain with a 16S rRNA sequence exhibiting at least 97%, more preferably 98%, even more preferably 99%, or 100% sequence identity to SEQ ID N° 1 and an isolated *A. oxydans* strain with a 16S rRNA sequence exhibiting at least 97%, more preferably 98%, even more preferably 99%, or 100% sequence identity to SEQ ID N° 2 whereas said *A. agilis* comprises a 16S rRNA sequence exhibiting at least 97% more preferably 98%, even more preferably 99%, or 100% sequence identity to SEQ ID N° 3. In another embodiment, said bacterial culture comprises an isolated *S. niveus* strain deposited as LMG P-29828 and an isolated *A. oxydans* strain deposited as LMG P-29827 and/or the isolated *A. agilis* accessible via CB-283399 CAJA 1-24.

Thus, in particular embodiments, a method is provided for enhancing growth and/or yield of a plant, said method comprising:
  inoculating a plant growth medium with the supernatant or with an extract of an enriched bacterial culture as described above, wherein said culture comprises an isolated *Streptomyces* strain, preferably an *S. niveus* strain and an isolated *Arthrobacter* strain, preferably *A. oxydans* or *agilis* strain;
  growing said plant in said medium;
  to enhance growth and/or yield of said plant.

Thus, in one embodiment, a method is provided for stimulating plant growth comprising applying the bacterial culture comprising an isolated *S. niveus* strain and an isolated *A. oxydans* and/or *agilis* strain or more particularly comprising an isolated *S. niveus* strain with a 16S rRNA sequence exhibiting at least 97%, more preferably 98%, even more preferably 99%, or 100% sequence identity to SEQ ID N° 1 and an isolated *A. oxydans* strain with a 16S rRNA sequence exhibiting at least 97% more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3 to a plant, plant part, plant seed or to the plant growth medium. In a more particular embodiment, said isolated *S. niveus* strain is the *S. niveus* strain deposited as LMG P-29828, said isolated *A. oxydans* strain is the *A. oxydans* strain deposited as LMG P-29827 and said the isolated *A. agilis* is accessible via CB-283399 CAJA 1-24. In the latter and further embodiments and aspects, "stimulating", "enhancing", "increasing" or "improving" refers to an at least 5% increase or at least 10% increase or at least 25% increase or at least 50% increase or at least 75% increase or at least a 100% increase in the property being measured (e.g. plant growth, plant yield).

In one embodiment, a method is provided for enhancing nutrient uptake and nutrient use efficiency of a plant, said method comprising:
  inoculating a plant growth medium with an enriched bacterial culture according to one of the embodiments as described above, wherein said culture comprises at least one *Streptomyces* strain, preferably an isolated *S. niveus* strain and an an *Arthrobacter* strain, preferably an isolated *A. oxydans* or *agilis* strain;
  growing a plant in said medium;
  to enhance nutrient uptake and nutrient use efficiency of said plant.

In a more particular extension of the latter embodiment, said isolated *S. niveus* strain comprises a 16S rRNA sequence exhibiting at least 97%, more preferably 98%, even more preferably 99%, or 100% sequence identity to SEQ ID N° 1 and said isolated *A. oxydans* strain comprises a 16S rRNA sequence exhibiting at least 97%, more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3. In another particular extension of the latter embodiment, said isolated *S. niveus* strain is the *S. niveus* strain deposited as LMG P-29828, said isolated *A. oxydans* strain is the *A. oxydans* strain deposited as LMG P-29827 and said isolated *A. agilis* is accessible via CB-283399 CAJA 1-24.

In another embodiment, a method is provided for enhancing nitrogen fixating capacities of a plant, said method comprising:
 inoculating a plant growth medium with an enriched bacterial culture according to one of the embodiments as described above, wherein said culture comprises at least an isolated *Streptomyces* strain, preferably an isolated *S. niveus* strain and at least an isolated *Arthrobacter* strain, preferably an isolated *A. oxydans* or *agilis* strain;
 growing a plant in said medium;
 to enhance the nitrogen fixating capacities of said plant.

In a more particular extension of the latter embodiment, said isolated *S. niveus* strain comprises a 16S rRNA sequence exhibiting at least 97%, more preferably 98%, even more preferably 99%, or 100% sequence identity to SEQ ID N° 1 and said isolated *A. oxydans* strain comprises a 16S rRNA sequence exhibiting at least 97%, more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3. In another particular extension of the latter embodiment, said isolated *S. niveus* strain is the *S. niveus* strain deposited as LMG P-29828, said isolated *A. oxydans* strain is the *A. oxydans* strain deposited as LMG P-29827 and said isolated *A. agilis* is accessible via CB-283399 CAJA 1-24.

The application also envisages the inoculation of the plant growth medium with the supernatant or with an extract of the described bacterial culture instead of inoculating with the bacterial culture itself.

In another embodiment, a method is provided for enhancing growth and/or yield and/or for enhancing nutrient uptake and nutrient use efficiency and/or for enhancing nitrogen fixating capacities of a plant, said method comprising applying an effective amount of one of the embodiments of the bacterial culture as described above to said plant or to said plant's surroundings. In a more particular extension of the latter embodiments, a combination of *S. niveus* with *A. oxydans* and/or *A. agilis* is provided. Said isolated *S. niveus* strain comprises a 16S rRNA sequence exhibiting at least 97%, more preferably 98%, even more preferably 99%, or 100% sequence identity to SEQ ID N° 1 and said isolated *A. oxydans* strain comprises a 16S rRNA sequence exhibiting at least 97%, more preferably 98%, even more preferably 99%, or 100% sequence identity to SEQ ID N° 2 whereas said *A. agilis* comprises a 16S rRNA sequence exhibiting at least 97% more preferably 98%, even more preferably 99%, or 100% sequence identity to SEQ ID N° 3.

In another particular extension of the latter embodiment, said isolated *S. niveus* strain is the *S. niveus* strain deposited as LMG P-29828 and said isolated *A. oxydans* strain is the *A. oxydans* strain deposited as LMG P-29827 and said isolated *A. agilis* is accessible via CB-283399 CAJA 1-24.

In a fourth aspect, a method is provided for enhancing plant growth and/or plant yield and/or for enhancing nutrient uptake and/or nutrient use efficiency and/or for enhancing nitrogen fixating capacities, said method comprising growing coated seeds of a plant, wherein said seeds are coated with an enriched bacterial culture according to one of the embodiments as described above, comprising at least an isolated *Streptomyces* strain, preferably a *Streptomyces niveus* strain and at least an isolated *Arthrobacter* strain, preferably an *A. oxydans* or *agilis* strain, to obtain enhanced growth and/or yield of said plant. This is equivalent as saying that a method is provided for enhancing growth and/or yield of a plant, said method comprising germinating seeds of said plant, wherein said seeds are coated with an enriched bacterial culture comprising at least an isolated *Streptomyces* strain, preferably, an isolated *Streptomyces niveus* strain and at least an isolated *Arthrobacter* strain, preferably an isolated *Arthrobacter oxydans* or *agilis* strain, to obtain enhanced growth and/or yield of said plant. In particular embodiments, said isolated *S. niveus* strain comprises a 16S rRNA sequence exhibiting at least 97%, more preferably 98%, even more preferably 99%, or 100% sequence identity to SEQ ID N° 1 and said isolated *A. oxydans* strain comprises a 16S rRNA sequence exhibiting at least 97%, more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3.

In a more particular embodiment, said isolated *S. niveus* strain is the *S. niveus* strain deposited as LMG P-29828 and said *A. oxydans* is the *A. oxydans* strain deposited as LMG P-29827 and said isolated *A. agilis* is accessible via CB-283399 CAJA 1-24. In another embodiment, a method is provided for enhancing growth and/or yield of a plant, said method comprising germinating seeds of said plant, wherein said seeds are dipped in an enriched bacterial culture according to one of the embodiments as described herein comprising at least an isolated *Streptomyces* strain, preferably an *S. niveus* strain and an at least an isolated *Arthrobacter* strain, preferably an *Arthrobacter oxydans* or *agilis* strain, to obtain enhanced growth and/or yield of said plant. In particular embodiments, said isolated *S. niveus* strain comprises a 16S rRNA sequence exhibiting at least 97%, more preferably 98%, even more preferably 99%, or 100% sequence identity to SEQ ID N° 1 and said isolated *A. oxydans* strain comprises a 16S rRNA sequence exhibiting at least 97%, more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3.

In a more particular embodiment, said isolated *S. niveus* strain is the *S. niveus* strain deposited as LMG P-29828 and said *A. oxydans* is the *A. oxydans* strain deposited as LMG P-29827 and said isolated *A. agilis* is accessible via CB-283399 CAJA 1-24. After seed dipping, the seeds can be sown immediately or first dried and then stored before sowing.

In some embodiments, after the coating procedure, the seeds should comprise at least one living cell of an isolated *Streptomyces* and at least one living cell of an *Arthrobacter* strain, by preference an isolated *Streptomyces niveus* strain and an isolated *A. oxydans* or *agilis* strain or more particularly one living cell of an isolated *S. niveus* strain with a 16S rRNA sequence exhibiting at least 97%, more preferably 98%, even more preferably 99%, or 100% sequence identity to SEQ ID N° 1 and one living cell of an isolated *A. oxydans* with a 16S rRNA sequence exhibiting at least 97%, more preferably 98%, even more preferably 99%, or 100% sequence identity to SEQ ID N° 2 whereas said *A. agilis* comprises a 16S rRNA sequence exhibiting at least 97% more preferably 98%, even more preferably 99%, or 100% sequence identity to SEQ ID N° 3 or even more particularly one living cell of an isolated *S. niveus* strain deposited as LMG P-29828 and one living cell of an isolated *A. oxydans* strain deposited as LMG P-29827 and/or isolated *A. agilis* is accessible via CB-283399 CAJA 1-24.

In other embodiments, after the coating procedure, the seeds should comprise at least an effective amount of one or more extracts of an isolated enriched bacterial culture according to an embodiment of the current invention, said culture comprises at least one *Streptomyces* strain, preferably an isolated *Streptomyces niveus* strain and at least one *Arthrobacter* strain, preferably an isolated *A. oxydans* or *agilis* strain. Thus, this application also provides a method for enhancing plant growth and/or plant yield, said method comprising growing coated seeds of a plant, wherein said seeds are coated with an effective amount of an extract of an enriched bacterial culture as described above, preferably comprising at least one isolated *Streptomyces* strain, preferably an isolated *Streptomyces niveus* strain and at least one isolated *Arthrobacter* strain, preferably an isolated *Arthrobacter oxydans* and/or *agilis* strain or more particularly comprising an isolated *S. niveus* strain with a 16S rRNA sequence exhibiting at least 97%, more preferably 98%, even more preferably 99%, or 100% sequence identity sequence identity to SEQ ID N° 1 and an isolated *A. oxydans* strain with a 16S rRNA sequence exhibiting at least 97%, more preferably 98%, even more preferably 99%, or 100% sequence identity sequence identity to SEQ ID N° 2, whereas said *A. agilis* comprises a 16S rRNA sequence exhibiting at least 97% more preferably 98%, even more preferably 99%, or 100% sequence identity to SEQ ID N° 3 or even more particularly comprising the isolated *S. niveus* strain deposited as LMG P-29828 and the isolated *A. oxydans* strain deposited as LMG P-29827 and said isolated *A. agilis* is accessible via CB-283399 CAJA 1-24, to obtain enhanced growth and/or yield of said plant. This is equivalent as saying that a method is provided for enhancing growth and/or yield of a plant, said method comprising germinating seeds of said plant, wherein said seeds are coated with an effective amount of an extract of an enriched bacterial culture comprising at least one isolated *Streptomyces* strain, preferably an isolated *Streptomyces niveus* strain and at least one isolated *Arthrobacter* strain, preferably an isolated *Arthrobacter oxydans* and/or *agilis* strain or more particularly comprising an isolated *S. niveus* strain with a 16S rRNA sequence exhibiting at least 97%, more preferably 98%, even more preferably 99%, or 100% sequence identity sequence identity to SEQ ID N° 1 and an isolated *A. oxydans* strain with a 16S rRNA sequence exhibiting at least 97%, more preferably 98%, even more preferably 99%, or 100% sequence identity sequence identity to SEQ ID N° 2, whereas said *A. agilis* comprises a 16S rRNA sequence exhibiting at least 97% more preferably 98%, even more preferably 99%, or 100% sequence identity to SEQ ID N° 3 or even more particularly comprising the isolated *S. niveus* strain deposited as LMG P-29828 and the isolated *A. oxydans* strain deposited as LMG P-29827 and said isolated *A. agilis* is accessible via CB-283399 CAJA 1-24, to obtain enhanced growth and/or yield of said plant.

In alternative embodiments, the current application also envisages that the plant seeds described in the embodiments of the fourth aspect, are coated with an extract of said bacterial culture instead of with said bacterial culture itself. Also, in other alternative embodiments, it is envisaged that the plant seeds described in the embodiments of the fourth aspect, are coated with the supernatant of said bacterial culture instead of with said bacterial culture itself.

In a fifth aspect, a method is provided for enhancing growth and/or yield of a plant, said plant may optionally be free of disease and/or pathogen pressure and/or pest organisms said method comprising:
  growing said plant in an environment that supports plant growth;
  administering a sprayable formulation to said environment or to said plant, said formulation comprising an enriched bacterial culture as described above, where said culture comprises at least an isolated *Streptomyces* strain, preferably a *S. niveus* strain and at least an isolated *Arthrobacter* strain, preferably an isolated *A. oxydans* and/or *agilis* strain;
to obtain enhanced growth and/or yield of said plant.

In a more particular extension of the latter embodiment, said isolated *S. niveus* strain comprises a 16S rRNA sequence exhibiting at least 97%, more preferably 98%, even more preferably 99%, or 100% sequence identity to SEQ ID N° 1 and said isolated *A. oxydans* strain comprises a 16S rRNA sequence exhibiting at least 97%, more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3. In another particular extension of the latter embodiment, said isolated *S. niveus* strain is the *S. niveus* strain deposited as LMG P-29828 and said isolated *A. oxydans* strain is the *A. oxydans* strain deposited as LMG P-29827 and said isolated *A. agilis* is accessible via CB-283399 CAJA 1-24.

In another embodiment, a method is provided for enhancing growth and/or yield of a plant, wherein said plant is grown in the absence of salt (NaCl) stress and wherein said method comprising:
  growing said plant in an environment that supports plant growth;
  administering a sprayable formulation to said environment or to said plant, said formulation comprising an enriched bacterial culture, where said culture comprises an isolated *Streptomyces niveus* strain and an isolated *A. oxydans* strain;
to obtain enhanced growth and/or yield of said plant in the absence of salt (NaCl) stress.

In another embodiment of this aspect, a method is provided for enhancing nutrient uptake and/or nutrient use efficiency of a plant, said method comprising:
  growing said plant in an environment that supports plant growth;
  administering a sprayable formulation to said environment or to said plant, said formulation comprising an enriched bacterial culture as described above, where said culture comprises at least an isolated *Streptomyces* strain, preferably a *Streptomyces niveus* strain and at least an isolated *Arthrobacter* strain, preferably an *A. oxydans* or *agilis* strain;
to obtain enhanced nutrient uptake and/or nutrient use efficiency of said plant.

In another embodiment, a method is provided for enhancing the nitrogen fixating capacities of a plant, said method comprising:
  growing said plant in an environment that supports plant growth;
  administering a sprayable formulation to said environment or to said plant, said formulation comprising an enriched bacterial culture as described above, where said culture comprises at least an isolated *Streptomyces* strain, preferably a *Streptomyces niveus* strain and at least an isolated *Arthrobacter* strain, preferably an *A. oxydans* or *agilis* strain;

to obtain enhanced nitrogen fixating capacities of said plant.

The above disclosed methods thus also includes irrigation with a liquid comprising an enriched bacterial culture, wherein said culture comprises at least one isolated *Streptomyces* strain, preferably an isolated *S. niveus* strain and at least an isolated *Arthrobacter* strain, preferably an isolated *A. oxydans* or *agilis* strain. In a more particular extension of the latter embodiment, said isolated *S. niveus* strain comprises a 16S rRNA sequence exhibiting at least 97%, more preferably 98%, even more preferably 99%, or 100% sequence identity to SEQ ID N° 1 and said isolated *A. oxydans* strain comprises a 16S rRNA sequence exhibiting at least 97%, more preferably 98%, even more preferably 99%, or 100% sequence identity to SEQ ID N° 2, whereas said *A. agilis* comprises a 16S rRNA sequence exhibiting at least 97% more preferably 98%, even more preferably 99%, or 100% sequence identity to SEQ ID N° 3.

More particular said culture comprises an isolated *S. niveus* strain deposited as LMG P-29828 and an isolated *A. oxydans* strain deposited as LMG P-29827 and/or isolated *A. agilis* is accessible via CB-283399 CAJA 1-24.

Hence, in various embodiments, a method is provided for enhancing growth and/or yield of a plant, said method comprising:
growing said plant in an environment that supports plant growth;
irrigating said environment using a liquid solution comprising an enriched bacterial culture, where said culture comprises an isolated *Streptomyces niveus* strain and an isolated *A. oxydans* strain;
to obtain enhanced growth and/or yield of said plant.

In a more particular embodiment, a method is provided for enhancing growth and/or yield of a plant, wherein said plant is free of disease and/or pathogen pressure and/or pest organisms, said method comprising:
growing said plant in an environment that supports plant growth;
irrigating said environment using a liquid solution comprising an enriched bacterial culture, where said culture comprises an isolated *Streptomyces niveus* strain and an isolated *A. oxydans* strain;
to obtain enhanced growth and/or yield of said plant.

Optionally, said plant may be grown in the absence of salt (NaCl) stress.

In more particular embodiments, methods are provided for enhancing nitrogen fixating capacities of a plant, said method comprising:
growing said plant in an environment that supports plant growth;
irrigating said environment using a liquid solution comprising an enriched bacterial culture as described above, where said culture comprises at least an isolated *Streptomyces* strain, preferably an isolated *Streptomyces niveus* strain and at least an *Arthrobacter* starin, preferably an isolated *A. oxydans* or *agilis* strain;
to obtain enhanced growth and/or yield of said plant.

In alternative embodiments, the current application also envisages that the sprayable formulation of the previous embodiments or the liquid for irrigation purposes of the above embodiments comprise an extract of said enriched bacterial culture or the supernatant of said culture instead of said bacterial culture itself.

In particular alternatives of the fifth aspect and of all of its accompanying above described embodiments, the *S. niveus* strain of said bacterial culture is an isolated *S. niveus* strain comprising a 16S rRNA sequence exhibiting at least 98% sequence identity to SEQ ID N° 1 and the *A. oxydans* strain of said bacterial culture is an isolated *A. oxydans* strain comprising a 16S rRNA sequence exhibiting at least 98% sequence identity to SEQ ID N° 2, whereas said *A. agilis* comprises a 16S rRNA sequence exhibiting at least 98% sequence identity to SEQ ID N° 3.

In other alternative versions of the fifth aspect and of all its accompanying above described embodiments, the *S. niveus* strain of said bacterial culture is an isolated *S. niveus* strain comprising a 16S rRNA sequence exhibiting at least 99% sequence identity to SEQ ID N° 1 and the *A. oxydans* strain of said bacterial culture is an isolated *A. oxydans* strain comprising a 16S rRNA sequence exhibiting at least 99% sequence identity to SEQ ID N° 2 whereas said *A. agilis* comprises a 16S rRNA sequence exhibiting at least 99% sequence identity to SEQ ID N° 3. In other alternative versions of the fifth aspect and of all its accompanying above described embodiments, the *S. niveus* strain of said bacterial culture is an isolated *S. niveus* strain comprising a 16S rRNA sequence exhibiting at least 100% sequence identity to SEQ ID N° 1 and the *A. oxydans* strain of said bacterial culture is an isolated *A. oxydans* strain comprising a 16S rRNA sequence exhibiting at least 100% sequence identity to SEQ ID N° 2 whereas said *A. agilis* comprises a 16S rRNA sequence exhibiting 100% sequence identity to SEQ ID N° 3. In other alternative versions of the fifth aspect and of all its accompanying above described embodiments, the *S. niveus* strain of said bacterial culture is the isolated *S. niveus* strain deposited as LMG P-29828 and the *A. oxydans* strain of said bacterial culture is the isolated *Arthrobacter oxydans* strain deposited as LMG P-29827 and said isolated *A. agilis* is accessible via CB-283399 CAJA 1-24.

The invention as described above is directed to the combination of at least one *Streptomyces* strain and at least one *Arthrobacter* strain and for the various purposes as explained. However, the current invention equally pertains to the individual isolated strains and their use for the purpose of enhancing plant growth and development.

In particular, the current invention is also directed to an isolated *Arthrobacter oxydans* strain deposited as LMG P-29827 or an isolated *Streptomyces niveus* deposited as LMG P-29827. This is equivalent as saying that an isolated *Arthrobacter oxydans* strain comprised in deposit LMG P-29827 is provided or an isolated *Streptomyces niveus* comprised in deposit LMG P-29827 is provided.

Said strain *Streptomyces niveus* comprises a 16S rRNA sequence exhibiting 100% sequence identity to the sequence depicted in SEQ ID N° 1 whereas *Arthrobacter oxydans* comprises a 16S rRNA sequence exhibiting 100% sequence identity to the sequence depicted in SEQ ID N° 2. This is equivalent as saying that said strains comprise a 16S rRNA sequence that is identical over the full length thereof to respectively SEQ ID N° 1 or SEQ ID N° 2.

In one embodiment, an enriched culture of an isolated *A. oxydans* strain deposited as LMG P-29827 or an enriched culture of an isolated *S. niveus* deposited as LMG P-29828 is provided.

In another embodiment, a bacterial culture is provided wherein said bacterial culture is enriched with the isolated *A. oxydans* strain deposited as LMG P-29827 or the isolated *S. niveus* strain as deposited as LMG-P-29828 and wherein "enriched" means that the total microbial population of said bacterial culture contains more than 50%, more than 60%, more than 70%, more than 80%, more than 90%, or more than 95% of said isolated strains.

In another embodiment, a biologically pure culture of the isolated *A. oxydans* strain deposited as LMG P-29827 or the isolated *S. niveus* strain as deposited as LMG-P-29828 is provided. As used herein, "biologically pure" refers to a culture which contains substantially no other microorganisms than the desired strains of microorganisms and thus a culture wherein virtually all of the cells present are of the selected strains. In practice, a culture is defined biologically pure if the culture contains at least more than 96%, at least more than 97%, at least more than 98% or at least more than 99% of the isolated strains of the current invention. When a biologically pure culture contains 100% of the desired microorganism a monoculture is reached. A monoculture thus only contains cells of the selected strain and is the most extreme form of a biologically pure culture.

In yet another embodiment, a supernatant is provided wherein said supernatant is obtained from a culture of the isolated *A. oxydans* strain deposited as LMG P-29827 or the isolated *S. niveus* strain as deposited as LMG-P-29828, wherein said culture can be an enriched culture of said strains or a biologically pure culture of said strains.

In yet another embodiment, an extract is provided wherein said extract is obtained from a culture of the isolated *A. oxydans* strain deposited as LMG P-29827 or the isolated *S. niveus* strain as deposited as LMG-P-29828, wherein said culture can be an enriched culture of said strains or a biologically pure culture of said strains.

In another embodiment, a composition comprising the isolated *A. oxydans* strain deposited as LMG P-29827 or the isolated *S. niveus* strain as deposited as LMG-P-29828 is provided. Also a composition is provided wherein said composition comprises one or more products derived from a culture of the isolated *A. oxydans* strain deposited as LMG P-29827 or the isolated *S. niveus* strain as deposited as LMG-P-29828. Said one or more products can be obtained from the supernatant or from an extract of said culture.

In another embodiment, a combination comprising the isolated *A. oxydans* strain deposited as LMG P-29827 or the isolated *S. niveus* strain as deposited as LMG-P-29828 and an agriculturally compatible carrier is provided. Also a combination is provided comprising an agriculturally compatible carrier and one or more products derived from a culture of the isolated *A. oxydans* strain deposited as LMG P-29827 or the isolated *S. niveus* strain as deposited as LMG-P-29828.

Thus in another embodiment, a plant seed or plant propagule coated with a microbial population comprising the *A. oxydans* strain deposited as LMG P-29827 or the isolated *S. niveus* strain as deposited as LMG-P-29828 is provided. This is equivalent as saying that a plant seed or plant propagule is provided, wherein said plant seed or propagule having applied to the surface of said seed or of said propagule, an enriched culture or biological pure culture of at least the *A. oxydans* strain deposited as LMG P-29827 or the isolated *S. niveus* strain as deposited as LMG-P-29828.

In a second aspect, a microbial population comprising an isolated *S. niveus* strain or *A. oxydans* strain comprising respectively a 16S rRNA sequence identical over the full length thereof to SEQ ID N° 1 or SEQ ID N° 2 is provided to enhance plant yield and/or plant growth. In one embodiment, a microbial population comprising the isolated *A. oxydans* strain deposited as LMG P-29827 or the *S. niveus* strain deposited as LMG P-29828 is provided to enhance plant yield and/or plant growth. This is equivalent as saying that a microbial population comprising said *A. oxydans* or *S. niveus* strain has plant growth promoting activity, as demonstrated in the Examples.

Thus in a more particular embodiment, a microbial population comprising an isolated *A. oxydans* strain comprising a 16S rRNA sequence identical over the full length thereof to SEQ ID N° 2 or comprising the isolated *A. oxydans* strain deposited as LMG P-29827, or an isolated *S. niveus* strain comprising a 16S rRNA sequence identical over the full length thereof to SEQ ID N° 1 or comprising the isolated *S. niveus* strain deposited as LMG P-29828 is provided to enhance plant yield.

In a more particular embodiment, a microbial population comprising an isolated *S. niveus* or *A. oxydans* strain comprising a 16S rRNA sequence identical over the full length thereof to respectively SEQ ID N° 1 or SEQ ID N° 2 or comprising the isolated *A. oxydans* strain or *S. niveus* strain deposited as respectively LMG P-29827 or LMG P-29828 is provided to enhance plant yield and/or plant growth in the absence of plant disease. Signs and symptoms of plant disease can be evaluated and interpreted by a person skilled in the art of plant pathology. Practitioners are particularly directed to Westcott's Plant Disease Handbook. Non-limiting examples of plant disease symptoms and signs are spots on leaves or on fruit, aberrant coloring of leaves, rot of leaves or fruit or roots, shoot or leaf blight, wilting, and presence of gals or tumors.

In an even more particular embodiment, a microbial population comprising an isolated *S. niveus* or *A. oxydans* strain comprising a 16S rRNA sequence identical over the full length thereof to respectively SEQ ID N° 1 or SEQ ID N° 2 or comprising the isolated *A. oxydans* strain or *S. niveus* strain deposited as LMG P-29827 or LMG P-29828 is provided to enhance plant yield and/or plant growth in the absence of pathogen pressure or in the absence of phytopathogenic organisms and/or pest organisms.

In an even more particular embodiment, a microbial population comprising the *A. oxydans* or *S. niveus* strains according to the current invention are provided to enhance plant yield and/or plant growth in the absence of salt (NaCl) stress. In an even more particular embodiment, said strains are provided to enhance plant yield and/or plant growth in the absence of drought stress.

In Example 3 of this application it is shown that the most significant plant growth promoting effect of the *S. niveus* and *A. oxydans* strain of the application is achieved in poor soil conditions. Indeed, the given soil is very low in nutrients essential for plant growth and development, especially in nitrate-nitrogen. Therefore and in yet another embodiment, a microbial population comprising an isolated *S. niveus* or *A. oxydans* strain is provided to increase nutrient uptake and/or nutrient use efficiency of a plant. In a more particular embodiment said isolated *A. oxydans* strain comprises a 16S rRNA sequence exhibiting at least 97%, at least 98%, at least 99%, or 100% sequence identity to SEQ ID N° 2 or the *A. oxydans* strain deposited as LMG P-29827, whereas the *S. niveus* strain comprises a 16S rRNA sequence exhibiting at least 97%, at least 98%, at least 99%, or 100% sequence identity to SEQ ID N° 1 or the *S. niveus* strain deposited as LMG P-29828.

In an even more particular embodiment, a microbial population comprising said strains according to the current invention are provided to increase nitrogen uptake and/or nitrogen use efficiency of a plant. In alternative embodiments said *A. oxydans* or *S. niveus* strain that increases nutrient uptake and/or nutrient use efficiency of a plant and/or nitrogen uptake and/or nitrogen use efficiency of a plant is either an isolated *A. oxydans* strain comprising a 16S rRNA sequence exhibiting at least 97%, at least 98%, at least 99%, at least 95% or 100% sequence identity to SEQ ID N° 2 or the *A. oxydans* strain deposited as LMG P-29827, whereas the *S. niveus* strain comprises a 16S rRNA sequence exhibiting at least 97%, at least 98%, at least 99%, or 100% sequence identity to SEQ ID N° 1 or the *S. niveus* strain deposited as LMG P-29828.

Second, to increase the efficiency of nutrient uptake, some plants possess mechanisms or structural features that provide advantages when growing in certain types of nutrient limited soils. One of the most universal adaptations to nutrient-limited soils is a change in root structure that may increase the overall surface area of the root to increase nutrient uptake or may increase elongation of the root system to access new nutrient sources. Administration of PGP bacteria can positively affect the root system (as demonstrated in this application) leading to an increase in the uptake of resources and a stimulation of overall plant growth. Thus in a particular embodiment, a microbial population comprising an isolated *A. oxydans* or *S. niveus* strain according to the current invention is provided to stimulate the growth of the plant's root system.

Supported by the experiments described in Example 3, the *S. niveus* and/or *A. oxydans* strain of the application is regarded a biofertilizer. Thus, in another embodiment, a microbial population comprising an isolated *S. niveus* or *A. oxydans* strain is provided for use as a biofertilizer. In an even more particular embodiment, a microbial population comprising either isolated *S. niveus* strain comprises a 16S rRNA sequence exhibiting at least 97%, more preferably 98%, even more preferably 99%, or 100% sequence identity to SEQ ID N° 1 or an isolated *A. oxydans* strain comprising a 16S rRNA sequence exhibiting at least 97%, at least 98%, at least 99%, or 100% sequence identity to SEQ ID N° 2 is provided for use as a biofertilizer. In a more particular embodiment a microbial population comprising either an isolated *A. oxydans* strain deposited as LMG P-29827 or an *S. niveus* strain deposited as LMG P-29828 is provided as biofertilizer.

In another embodiment, a microbial population comprising an isolated *A. oxydans* or *S. niveus* strain according to the current invention is provided to increase the nutrient uptake and/or nutrient use efficiency of a plant, wherein said plant is not a leguminous plant. As a more particular extension of the latter embodiment, said nutrient is selected from nitrogen, potassium and phosphorus. In an even more particular extension of the latter embodiment, said nutrient is nitrogen.

In another embodiment, a microbial population comprising an isolated *A. oxydans* or *S. niveus* strain is provided to increase the nitrogen fixating capacities of a plant.

Plant growth promoting microorganisms as isolated *A. oxydans* strains or *S. niveus* strains of the current invention can positively affect the relationship between nitrogen-fixing bacteria and the plant resulting in an increased transfer of organic nitrogen towards the plant and an overall increase in plant growth.

Plant growth promoting microorganisms produce compounds which can be secreted in the bacterial medium or can be stored in the cells. Therefore, in alternative embodiments the use of a supernatant or of an extract of the bacterial culture comprising an isolated *A. oxydans* or *S. niveus* strain is provided to enhance plant growth and/or yield. In more particular embodiments, the use of a supernatant or of an extract of the bacterial culture comprising an isolated *A. oxydans* or *S. niveus* strain according to the current invention is provided to enhance nutrient uptake and/or nutrient use efficiency of a plant. In even more particular embodiment, the use of a supernatant or of an extract of the microbial culture comprising an isolated *A. oxydans* or *S. niveus* strain is provided to increase the nitrogen fixating capacities of a plant.

In all above described embodiments of this second aspect, "enhance" or increase" or "improvement" refers to an at least 5% increase or at least 10% increase or at least 25% increase or at least 50% increase or at least 75% increase or at least a 100% increase in the property being measured. In particular alternatives of all above described embodiments of this second aspect, said isolated *A. oxydans* strain is an isolated *A. oxydans* strain comprising a 16S rRNA sequence exhibiting at least 97%, at least 98%, at least 99%, or 100% sequence identity to SEQ ID N° 2. In even more particular alternatives of all above described embodiments of this second aspect, said isolated *A. oxydans* strain is an isolated *A. oxydans* strain deposited as LMG P-29827.

Said isolated *S. niveus* strain is an isolated *S. niveus* strain comprising a 16S rRNA sequence exhibiting at least 97%, at least 98%, at least 99%, or 100% sequence identity to SEQ ID N° 1. In even more particular alternatives of all above described embodiments of this aspect, said isolated *S. niveus* strain is an isolated strain deposited as LMG P-29828.

In a third aspect, a method is provided for enhancing plant growth and/or plant yield, said method comprising:
 inoculating a plant growth medium with a microbial population, wherein said population comprises an isolated *A. oxydans* strain or an *S. niveus* strain;
 growing a plant in said medium;
to enhance growth and/or yield of said plant.

In one embodiment, said *A. oxydans* strain comprises a 16S rRNA sequence identical over the full length thereof to SEQ ID N° 2. In another embodiment, said *A. oxydans* strain is the *A. oxydans* strain deposited as LMG P-29827. Said isolated *S. niveus* strain is an isolated *S. niveus* strain comprising a 16S rRNA sequence exhibiting at least 97%, at least 98%, at least 99%, or 100% sequence identity to SEQ ID N° 1. In even more particular alternatives of all above described embodiments of this second aspect, said isolated *S. niveus* strain is an isolated strain deposited as LMG P-29828.

In a particular embodiment, a method is provided for enhancing growth and/or yield of a plant, wherein said plant is free of disease and/or pathogen pressure and/or pest organisms, said method comprising:
 inoculating a plant growth medium with a microbial population, wherein said population comprises an isolated *A. oxydans* strain or an isolated *S. niveus* strain as described above;
 growing said plant in said medium;
to enhance growth and/or yield of said plant.

The application also envisages the inoculation of the plant growth medium with the supernatant or with an extract of the bacterial culture comprising an isolated *A. oxydans* strain or *S. niveus* according to the current invention. Thus, in particular embodiments, a method is provided for enhancing growth and/or yield of a plant, said method comprising:
 inoculating a plant growth medium with the supernatant or with an extract of a bacterial population, wherein said population comprises an isolated *A. oxydans* strain or *S. niveus* as described above;
 growing said plant in said medium;
to enhance growth and/or yield of said plant. In more particular embodiments, said plant is a plant free of disease and/or pathogen pressure and/or pest organisms.

In even more particular embodiments, said *A. oxydans* strain comprises a 16S rRNA sequence identical over the full length thereof to SEQ ID N° 2. In another embodiment, said *A. oxydans* strain is the isolated *A. oxydans* strain deposited as LMG P-29827.

Said isolated *S. niveus* strain is an isolated *S. niveus* strain comprising a 16S rRNA sequence exhibiting at least 97%, at least 98%, at least 99%, or 100% sequence identity to SEQ ID N° 1. In even more particular alternatives of all above described embodiments of this second aspect, said isolated *S. niveus* strain is an isolated strain deposited as LMG P-29828.

Thus, in one embodiment, a method is provided for stimulating plant growth comprising applying the microbial culture comprising an isolated *A. oxydans* or *S. niveus* strain according to the current invention to a plant, plant part, plant seed or to the plant growth medium.

In one embodiment, a method is provided for enhancing nutrient uptake and nutrient use efficiency of a plant, said method comprising:
inoculating a plant growth medium with a microbial population, wherein said population comprises an isolated *A. oxydans* or *S. niveus* strain as described above;
growing a plant in said medium;
to enhance nutrient uptake and nutrient use efficiency of said plant.

In another embodiment, a method is provided for enhancing nitrogen fixating capacities of a plant, said method comprising:
inoculating a plant growth medium with a microbial population, wherein said population comprises an isolated *A. oxydans* strain or *S. niveus* strain;
growing a plant in said medium;
to enhance the nitrogen fixating capacities of said plant.

The application also envisages the inoculation of the plant growth medium with the supernatant or with an extract of the bacterial culture comprising an isolated *A. oxydans* strain or *S. niveus*, instead of inoculating with the bacterial population itself.

In another embodiment, a method is provided for enhancing growth and/or yield of a plant, said method comprising applying an effective amount of an isolated *A. oxydans* or *S. niveus* strain to said plant or to said plant's surroundings. In another embodiment, a method is provided for enhancing nutrient uptake and nutrient use efficiency of a plant, said method comprising applying an effective amount of an isolated *A. oxydans* or *S. niveus* strain to said plant or to said plant's surroundings. In another embodiment, a method is provided for enhancing nitrogen fixating capacities of a plant, said method comprising applying an effective amount of an isolated *A. oxydans* or *S. niveus* strain to said plant or to said plant's surroundings.

In particular alternatives of all embodiments of the above described aspect, said *A. oxydans* strain is an isolated *A. oxydans* strain comprising a 16S rRNA sequence exhibiting at least 97%, at least 98%, at least 99%, at least 99.5% or 100% sequence identity to SEQ ID N° 2 or in even more particular alternatives, said *A. oxydans* is the isolated *A. oxydans* deposited as LMG P-29827. Said isolated *S. niveus* strain is an isolated *S. niveus* strain comprising a 16S rRNA sequence exhibiting at least 97%, at least 98%, at least 99%, or 100% sequence identity to SEQ ID N° 1. In even more particular alternatives of all above described embodiments of this second aspect, said isolated *S. niveus* strain is an isolated strain deposited as LMG P-29828.

In a further aspect, a method is provided for enhancing plant growth and/or plant yield, said method comprising growing coated seeds of a plant, wherein said seeds are coated with a microbial population comprising an isolated *A. oxydans* or an *S. niveus* strain as described above by means of 16S rRNA sequence and/or deposit.

By preference, said isolated *S. niveus* or *A. oxydans* strain comprises a 16S rRNA sequence identical over the full length thereof respectively to SEQ ID N° 1 or SEQ ID N° 2 or comprising an isolated *A. oxydans* strain deposited as LMG P-29827 or an isolated *S. niveus* strain deposited as LMG P-29828, to obtain enhanced growth and/or yield of said plant.

In particular embodiments, said isolated *A. oxydans* strain is an isolated *A. oxydans* strain comprising a 16S rRNA sequence exhibiting at least 97%, at least 98%, at least 99%, at least 99.5% or 100% sequence identity to SEQ ID N° 2.

In particular embodiments, said isolated *S. niveus* strain is an isolated *S. niveus* strain comprising a 16S rRNA sequence exhibiting at least 97%, at least 98%, at least 99%, at least 99.5% or 100% sequence identity to SEQ ID N° 1.

In another embodiment, a method is provided for enhancing growth and/or yield of a plant, said method comprising germinating seeds of said plant, wherein said seeds are dipped in a microbial population comprising an isolated *A. oxydans* or *S. niveus* strain as described above, to obtain enhanced growth and/or yield of said plant.

After seed dipping, the seeds can be sown immediately or first dried and then stored before sowing.

In some embodiments, after the coating procedure, the seeds should comprise at least one living cell of said isolated *A. oxydans* or *S. niveus* strain. In other embodiments, after the coating procedure, the seeds should comprise at least an effective amount of one or more extracts of a culture of said isolated *A. oxydans* or *S. niveus* strain. Thus, this application also provides a method for enhancing plant growth and/or plant yield, said method comprising growing coated seeds of a plant, wherein said seeds are coated with an effective amount of an extract of a bacterial population comprising an isolated *A. oxydans* or *S. niveus* strain, to obtain enhanced growth and/or yield of said plant. This is equivalent as saying that a method is provided for enhancing growth and/or yield of a plant, said method comprising germinating seeds of said plant, wherein said seeds are coated with an effective amount of an extract of a bacterial population comprising an isolated *A. oxydans* or *S. niveus* strain, to obtain enhanced growth and/or yield of said plant.

In another embodiment, a method is provided for enhancing nutrient uptake and/or nutrient use efficiency of a plant, said method comprising growing coated seeds of a plant, wherein said seeds are coated with a microbial population comprising an isolated *A. oxydans* or *S. niveus* strain, to obtain enhanced nutrient uptake and/or nutrient use efficiency of said plant. In another embodiment, a method is provided for enhancing the nitrogen fixating capacities of a plant, said method comprising growing coated seeds of a plant, wherein said seeds are coated with a microbial population comprising an isolated *A. oxydans* or *S. niveus* strain, to obtain enhanced nitrogen fixating capacities of said plant. In alternative embodiments, the current application also envisages that the plant seeds described in the embodiments of the fourth aspect, are coated with an extract of a bacterial culture of an isolated *A. oxydans* or *S. niveus* strain instead of with said bacterial population itself. Also, in other alternative embodiments, it is envisaged that the plant seeds described in the embodiments of the fourth aspect, are coated with the supernatant of a bacterial culture of an isolated *A. oxydans* or *S. niveus* strain instead of with said bacterial population itself.

In a fifth aspect, a method is provided for enhancing growth and/or yield of a plant, said method comprising:
- growing said plant in an environment that supports plant growth;
- administering a sprayable formulation to said environment or to said plant, said formulation comprising an isolated *A. oxydans* strain or an *S. niveus*;

to obtain enhanced growth and/or yield of said plant.

In one embodiment, a method is provided for enhancing growth and/or yield of a plant, wherein said plant is free of disease and/or pathogen pressure and/or pest organisms, said method comprising:
- growing said plant in an environment that supports plant growth;
- administering a sprayable formulation to said environment or to said plant, said formulation comprising an isolated *A. oxydans* or *S. niveus* strain;

to obtain enhanced growth and/or yield of said plant.

In another embodiment of this aspect, a method is provided for enhancing nutrient uptake and/or nutrient use efficiency of a plant, said method comprising:
- growing said plant in an environment that supports plant growth;
- administering a sprayable formulation to said environment or to said plant, said formulation comprising an isolated *A. oxydans* or *S. niveus* strain;

to obtain enhanced nutrient uptake and/or nutrient use efficiency of said plant.

In another embodiment, a method is provided for enhancing the nitrogen fixating capacities of a plant, said method comprising:
- growing said plant in an environment that supports plant growth;
- administering a sprayable formulation to said environment or to said plant, said formulation comprising an isolated *A. oxydans* or *S. niveus* strain;

to obtain enhanced nitrogen fixating capacities of said plant.

Hence, in various embodiments, a method is provided for enhancing growth and/or yield of a plant, said method comprising:

growing said plant in an environment that supports plant growth;

irrigating said environment using a liquid solution comprising an isolated *A. oxydans* or *S. niveus* strain;

to obtain enhanced growth and/or yield of said plant.

In a more particular embodiment, a method is provided for enhancing growth and/or yield of a plant, wherein said plant is free of disease and/or pathogen pressure and/or pest organisms, said method comprising:

growing said plant in an environment that supports plant growth;

irrigating said environment using a liquid solution comprising an isolated *A. oxydans* or *S. niveus* strain;

to obtain enhanced growth and/or yield of said plant.

In other embodiments, methods are provided for enhancing nutrient uptake and/or nutrient use efficiency of a plant, said method comprising:

growing said plant in an environment that supports plant growth;

irrigating said environment using a liquid solution comprising an isolated *A. oxydans* or *S. niveus* strain;

to obtain enhanced growth and/or yield of said plant.

In more particular embodiments, methods are provided for enhancing nitrogen fixating capacities of a plant, said method comprising:

growing said plant in an environment that supports plant growth;

irrigating said environment using a liquid solution comprising an isolated *A. oxydans* or *S. niveus* strain;

to obtain enhanced growth and/or yield of said plant.

In alternative embodiments, the current application also envisages that the sprayable formulation of the previous embodiments or the liquid for irrigation purposes of the above embodiments comprise an extract of a culture of an isolated *A. oxydans* or *S. niveus* strain or the supernatant of said culture instead of said strain itself.

In even more particular alternative embodiments, the said isolated *A. oxydans* strain of the above described embodiments of the fifth aspect is an isolated *A. oxydans* strain comprising a 16S rRNA sequence exhibiting at least 97%, at least 98%, at least 99%, at least 99.5% or 100% sequence identity to SEQ ID N° 1. In even more particular alternative embodiments, the said isolated *A. oxydans* strain of the above described embodiments of the fifth aspect is an isolated *A. oxydans* strain deposited as LMG P-29827. In particular embodiments, said isolated *S. niveus* strain is an isolated *S. niveus* strain comprising a 16S rRNA sequence exhibiting at least 97%, at least 98%, at least 99%, at least 99.5% or 100% sequence identity to SEQ ID N° 1.

The invention can be summarized in the following embodiments:

For *Streptomyces:*

1. An isolated *Streptomyces* strain comprising a 16S rRNA sequence exhibiting at least 99.1% sequence identity to SEQ ID N° 1.

2. The bacterial strain of embodiment 1, wherein said isolated *Streptomyces* strain is a *Streptomyces niveus* strain comprising a 16S rRNA sequence exhibiting at least 99.1% sequence identity to SEQ ID N° 1.

3. The bacterial strain of embodiment 1 or 2, wherein said isolated *Streptomyces* strain is comprised in deposit LMG P-29828.

4. An enriched culture of the bacterial strain according to anyone of the embodiments 1 to 3.

5. A supernatant obtained from a culture of the bacterial strain according to anyone of the embodiments 1 to 3.

6. An extract obtained from a culture of the bacterial strain according to anyone of the embodiments 1 to 3.

7. A combination comprising the bacterial strain according to anyone of the embodiments 1 to 3 and an agriculturally compatible carrier.

8. A plant seed coated with a microbial population comprising the bacterial strain according to anyone of the embodiments 1 to 3.

9. Use of a microbial population comprising the bacterial strain according to anyone of the embodiments 1 to 3 or an isolated *Streptomyces niveus* strain to enhance plant yield and/or plant growth.

10. Use of a microbial population comprising the bacterial strain according to anyone of the embodiments 1 to 3 or an isolated *Streptomyces niveus* strain to increase nutrient uptake and/or nutrient use efficiency of a plant.

11. Use of a microbial population comprising the bacterial strain according to anyone of the embodiments 1 to 3 or an isolated *Streptomyces niveus* strain to increase the nitrogen fixating capacities of a plant.

12. A method for enhancing growth and/or yield of a plant comprising:

inoculating a plant growth medium with a microbial population, wherein said population comprises the bacterial strain according to anyone of the embodiments 1 to 3 or an isolated *Streptomyces niveus* strain;

growing a plant in said plant growth medium;

to enhance growth and/or yield of said plant.

13. The method of embodiment 12, wherein the microbial population is applied to the plant growth medium as a powder, as a pellet, as a granule, as a liquid.

14. A method for enhancing growth and/or yield of a plant, said method comprising growing coated seeds of a plant, wherein said seeds are coated with a microbial population comprising the bacterial strain according to anyone of the embodiments 1 to 3 or an isolated *Streptomyces niveus* strain, to obtain enhanced growth and/or yield of said plant.

15. A method for enhancing growth and/or yield of a plant comprising:
  growing a plant in an environment that supports plant growth;
  administering a sprayable formulation to said environment or to said plant, said formulation comprising the bacterial strain according to anyone of the embodiments 1 to 3 or an isolated *Streptomyces niveus* strain;
to obtain enhanced growth and/or yield of said plant.

For *Arthrobacter*:

1. An isolated *Arthrobacter oxydans* strain deposited as LMG P-29827.

2. An enriched culture of the bacterial strain of embodiment 1.

3. A supernatant obtained from a culture of the bacterial strain of embodiment 1.

4. An extract obtained from a culture of the bacterial strain of embodiment 1.

5. A combination comprising the bacterial strain of embodiment 1 and an agriculturally compatible carrier.

6. A plant seed coated with a microbial population comprising the bacterial strain of embodiment 1.

7. Use of a microbial population comprising an isolated *Arthrobacter oxydans* strain to enhance plant yield and/or plant growth, wherein said strain comprises a 16S rRNA sequence that is identical over the full length thereof to SEQ ID N° 2.

8. Use of a microbial population comprising the bacterial strain of embodiment 1 to enhance plant yield and/or plant growth.

9. Use of a microbial population comprising an isolated *Arthrobacter oxydans* strain to increase nutrient uptake and/or nutrient use efficiency of a plant, wherein said strain preferably comprises a 16S rRNA sequence that is identical over the full length thereof to SEQ ID N° 2.

10. Use of a microbial population comprising an isolated *Arthrobacter oxydans* strain to increase the nitrogen fixating capacities of a plant.

11. A method for enhancing growth and/or yield of a plant comprising:
  inoculating a plant growth medium with a microbial population, wherein said population comprises the bacterial strain of embodiment 1;
  growing a plant in said plant growth medium;
to enhance growth and/or yield of said plant.

12. The method of embodiment 11, wherein the microbial population is applied to the plant growth medium as a powder, as a pellet, as a granule, as a liquid.

13. A method for enhancing growth and/or yield of a plant, said method comprising growing coated seeds of a plant, wherein said seeds are coated with a microbial population comprising the bacterial strain of embodiment 1, to obtain enhanced growth and/or yield of said plant.

14. A method for enhancing growth and/or yield of a plant comprising:
  growing a plant in an environment that supports plant growth;
  administering a sprayable formulation to said environment or to said plant, said formulation comprising the bacterial strain of embodiment 1;
to obtain enhanced growth and/or yield of said plant.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application.

EXAMPLES

Example 1: Inoculation of Maize Seedlings to Select Candidate Bacterial Inoculants In order to screen for microorganisms that stimulate plant growth and/or performance, a large collection of carefully selected bacterial strains was used. The collection was obtained from Fundación MEDINA (Granada Spain; http://www.medinadiscovery.com/home). As a primary screen to identify candidate bacterial strains that enhance maize juvenile growth, we have developed a sand-perlite screening assay. In this primary screen 230 bacterial strains were used. Maize hybrid seeds (Limagrain, LG30.218) were sterilized with an ethanol/bleach procedure and germinated on $H_2O$+ AGAR plates. Equally germinated seedlings after 48 h were selected for bacterial inoculation and mock inoculation (no bacteria). Seedlings were inoculated for 3 h on a shaker in the bacterial and mock solution before transferring them to a sand/perlite set up. For the sand/perlite assay first a sand/perlite mix was prepared that consists of 1:1 sand: perlite ratio, saturated with water. Subsequently, 15 plastic pots were filled with an equal amount of the sand/perlite mix. Mock and inoculated seedlings were transferred to the pots with sand/perlite mix. The trays were kept at 23 degrees, long day light regime and humidity of 55%. Every other day, a tray with 15 plants receives 300 ml $H_2O$. Once a week the water was replaced by 0.5 diluted HS solution (see materials and methods for recipe). Plants were evaluated after three weeks of growth for root and shoot fresh biomass weight. The sand/perlite assay generated robust and repeatable results: out of a total of 23 repeated experiments, the vast majority confirmed the effects (positive, neutral or negative for fresh root and shoot biomass, $p<0.05$). Candidate strains that showed positive effects on one of the investigated parameters were repeated.

Figure 2:
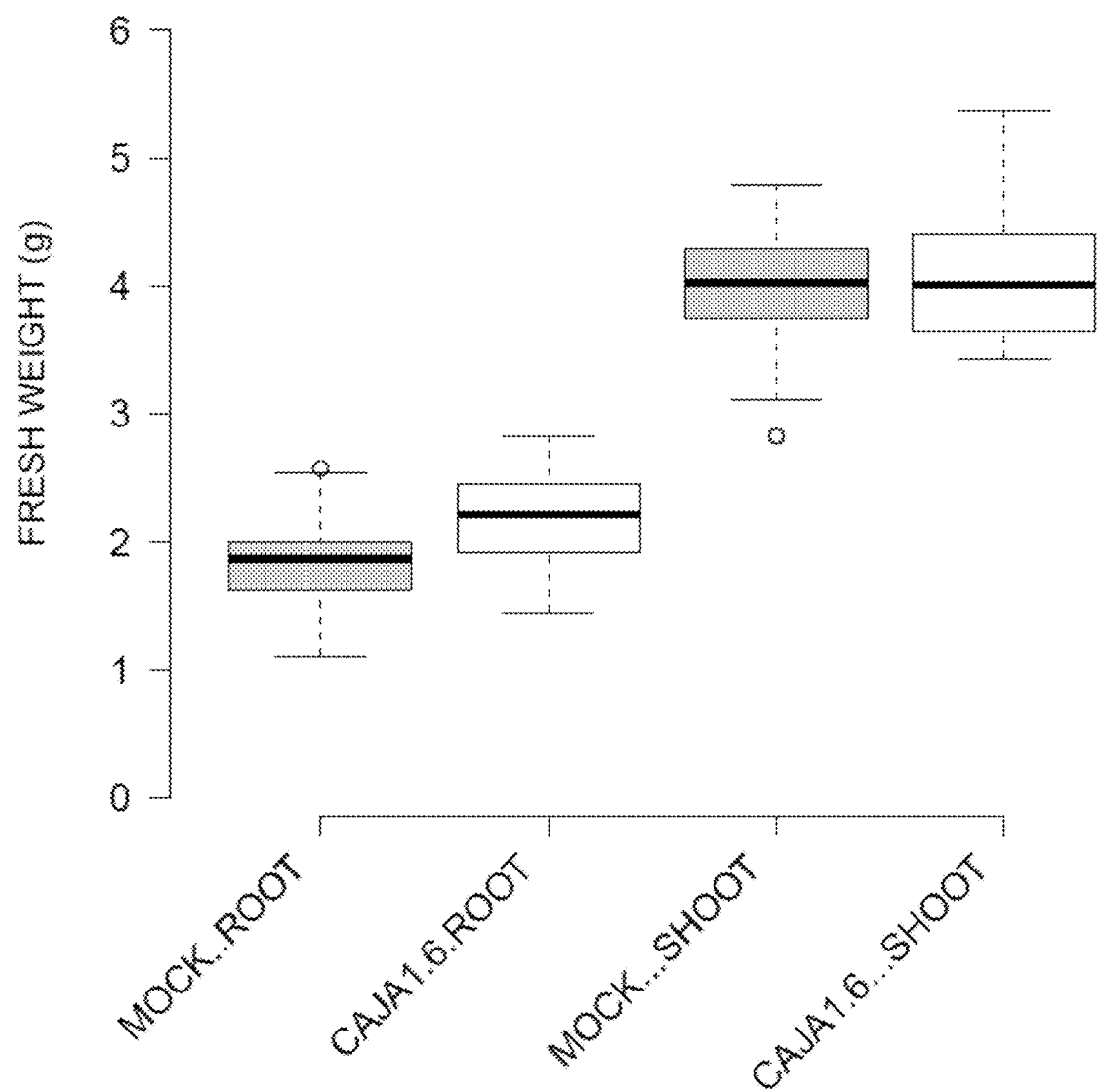

For further research we selected strains CA-227571, CB-278407 and CB-283399. FIG. 1 shows merged data of two repeats of CA-227571 in the sand/perlite screening. We have observed a repeatable significant increase in the root fresh weight. Inoculation of maize seedlings with CA-227571 resulted in an increase of root fresh weight of 27% ($p<0.01$). FIG. 2 shows merged data of two repeats of CB-278407 in the sand/perlite screening. We have observed a repeatable significant increase in the root fresh weight.

Inoculation of maize seedlings with CB-278407 resulted in an increase of root fresh weight of 17% ($p<0.01$).

Example 2: CA-227571 and CB-278407 Isolation and Cultivation

Strain CA-227571 was isolated from the rhizosphere soil of a specimen of *Astragalus captiosus* growing in a river bank of the Tergi river in Kazbegi, Republic of Georgia. The soil suspension (10 mg/ml) was serially diluted and plated on glycerol/NZ amine based agar and incubated for 4 weeks at 28° C. prior to isolation. The CA-227571 strain was purified and maintained in ISP-2 agar and cultivated in ATCC-2 medium to be preserved as fresh frozen stocks in 10% glycerol. To cultivate the CA-227571 strain, the ATCC-2 bacterial growth medium was used. Fresh inoculants were first prepared from frozen glycerol stocks (−70° C.) on solid growth medium (bacterial agar), after which a liquid culture was initiated from these agar plates. Liquid cultures were grown at 28° C., while shaking for 3 days.

Next to strain CA-227571, another strain with putative plant growth promoting effects was isolated, more particularly strain CB-278407. Strain CB-278407 was isolated from a soil sample collected under *Quercus ilex* at the Embalse de Canales, Pinos Genil, Spain, using VL-70 bacterial isolation agar medium supplemented with 0.5 mM xylose (Schoenborn L, Yates P S, Grinton B E, Hugenholtz P, Janssen P H (2004) Appl Environ Microbiol 70:4363-4366), and purified on R2A agar. To cultivate the CB-278407 strains, the TSB bacterial growth medium was used. Fresh inoculants were first prepared from frozen glycerol stocks (−70° C.) on solid growth medium (bacterial agar), after which a liquid culture was initiated from these agar plates. Liquid cultures were grown at 28 degrees, while shaking for 1 day.

Strain CB-283399 was isolated from a soil sample obtained below a specimen of a *Thymus* sp. bush. The soil was collected in June 2012 in Albuñuelas, Granada, Spain (36° 56 N 3° 37'W) at 673 m altitude and maintained in cold room until used for isolation. The soil sample was dispersed in sterile VL70 salts medium by stirring with a magnetic bar, and 1/10 dilutions plated on gellan gum-solidified VL70 medium containing substrate D-xylose, 0.05% (w/v) (Sait et al. 2002; Joseph et al. 2003; Davis et al. 2005). Plates were incubated at 18° C. and 60% relative humidity in the dark up to two weeks. Strain CB-283399 was isolated and purified onto R2A agar medium, and cell suspensions in R2A medium were preserved as frozen stock in 20% glycerol.

Example 3: Performance of CA-227571 Coated Maize Plants in Soil

In the next step, the effect of CA-227571 was tested on maize plants grown in field soil. The setup of this assay is identical to the maize sand/perlite screening (see Example 1), with the only difference that sand/perlite was replaced by soil collected from the field. The soil was a rich, frequently fertilized soil with a nitrate-nitrogen ($NO_3$—N) concentration of 18.48 mg per kg soil dry weight, which is equivalent to a nitrate ($NO_3$) concentration of 81.8 mg per kg soil dry weight. $NO_3$—N refers to the weight of only the nitrogen atom within the nitrate molecule, whereas the nitrate-ion ($NO_3$) describes the weight of the entire nitrate molecule.

Figure 3:
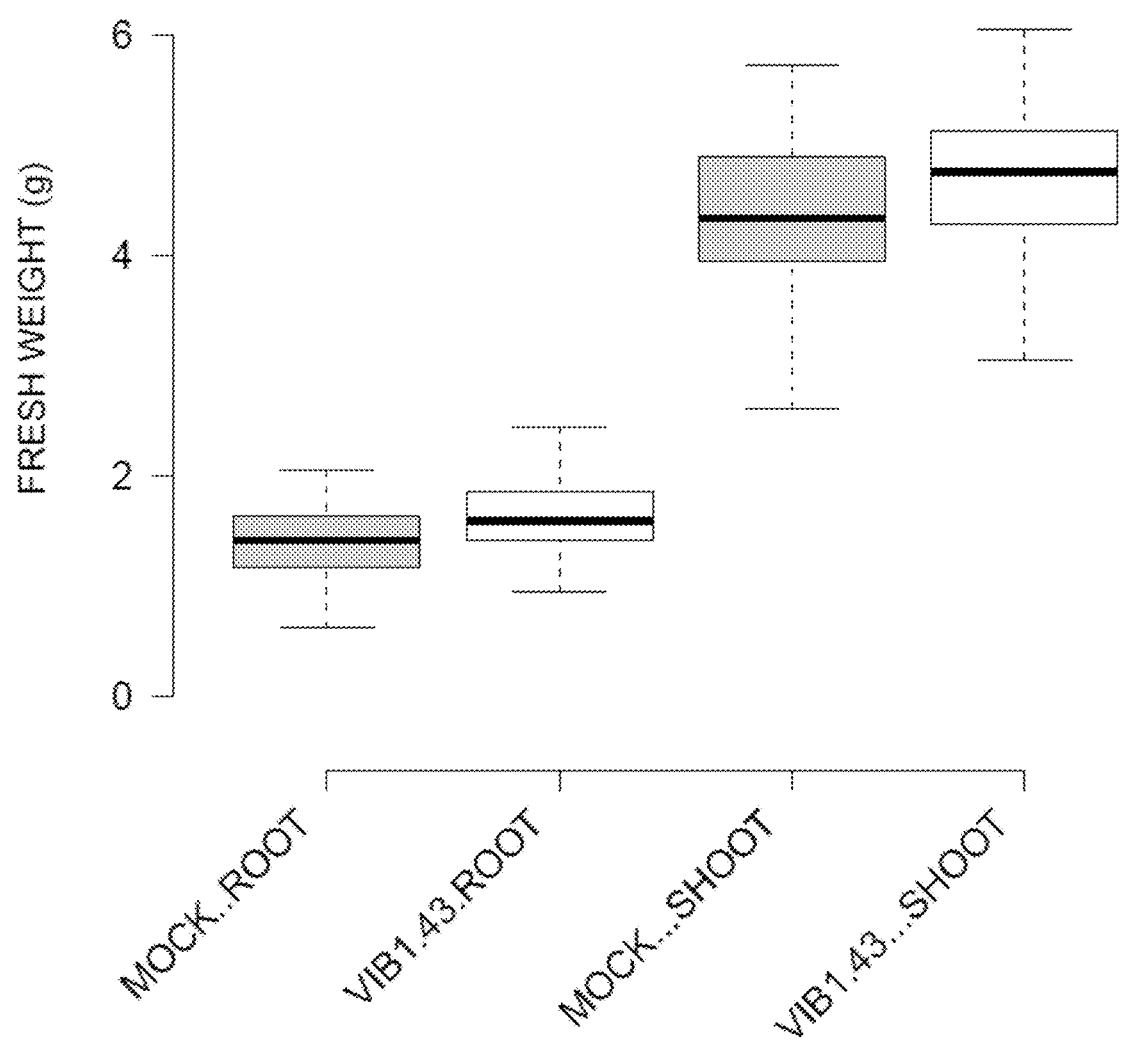

FIG. 3 shows merged data of three repeats of CA-227571 in the field soil screening. For this strain, we have observed a repeatable significant increase in both the root fresh weight and shoot fresh weight. Inoculation with CA-227571 of maize seedlings grown in field soil resulted in root fresh weight increase of 18% ($p<0.01$) and a shoot fresh weight of 7% ($p<0.05$).

To confirm the growth promoting capacity of CA-227571, we then tested the effect of CA-227571 inoculation in poor soil conditions. This poor soil is characterized by a $NO_3$—N concentration of less than 5 mg per kg soil dry weight. Maize hybrid seeds (Limagrain, LG30.218) were sterilized with an ethanol/bleach procedure and germinated on $H_2O$+AGAR plates. Equally germinated seedlings after 48 h were selected for bacterial inoculation and mock inoculation. Seedlings were inoculated for 3 h on a shaker in the bacterial and mock solution. The growth of the maize seedlings was analyzed on the Phenovision platform. Therefore, 19 Phenovision pots are filled with an equal amount of soil (700 g). For this assay, we used a commercial soil, low in N and frequently used for research purposes. After 3 h inoculation, mock and inoculated seedlings were transferred to the pots with soil. Humidity was maintained on the platform to a constant level, pots were weighed every day on the automatic Phenovision platform and watered to a desired soil humidity of 2.4 (g $H_2O$/g dried soil). Plants were evaluated after three weeks of growth for root and shoot fresh biomass weight, leaf 3 and leaf 4 leaf length.

Figure 4:
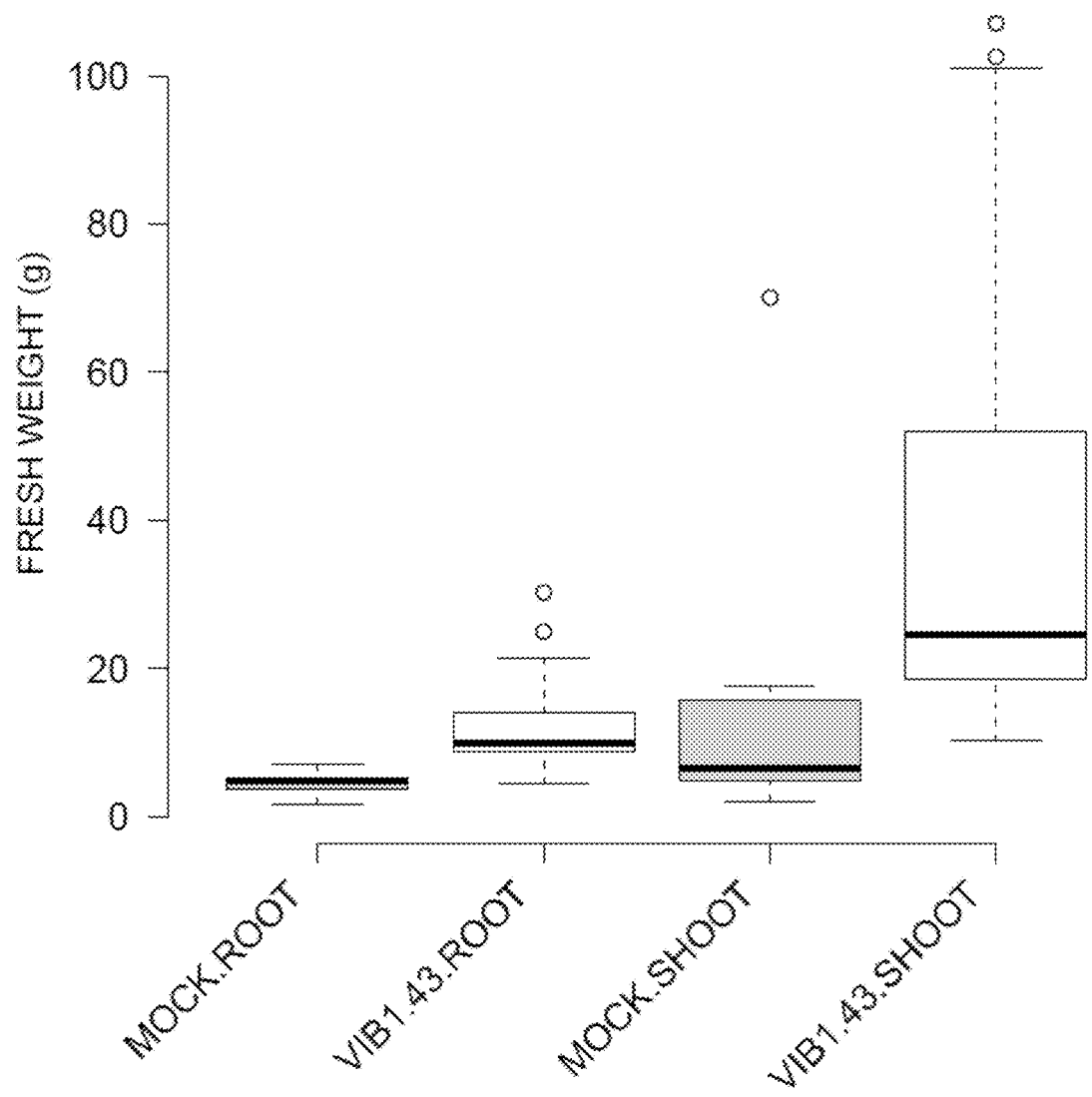
Figure 5:
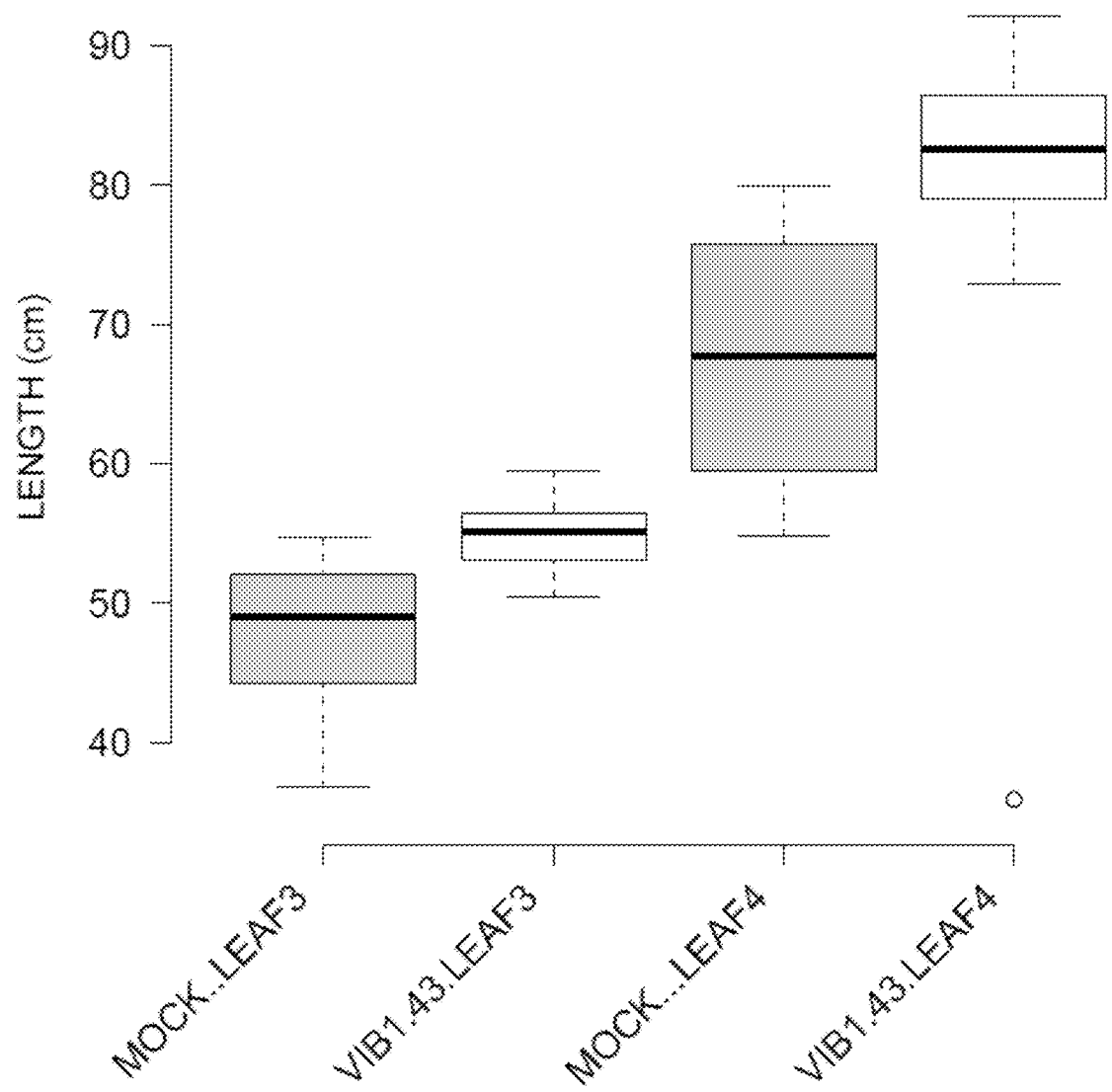

FIG. 4 shows the results for fresh root and shoot weight in the Phenovision screening. A significant increase in the root fresh weight was observed for the CA-227571 inoculated maize seedlings. Root fresh weight increases with 180% for CA-227571 inoculation ($p<0.01$), while shoot fresh weight increases with 240% for CA-227571 ($p<0.01$). FIG. 5 shows the results for the length of leaf 3 and leaf 4 in the Phenovision screening. For CA-227571 inoculation, we have observed a significant increase in length of both leaf 3 and leaf 4. Leaf 3 length increased with 15% ($p<0.01$), while leaf 4 length increased with 19% ($p<0.01$).

Example 4: Performance of CA-227571 Coated Wheat Seeds in Soil

In the final step, CA-227571 was tested for growth promotion on wheat juvenile growth. 20 falcon tubes were filled with an equal amount (80 g) of field soil (see Example 3) and watered with 10 ml $H_2O$. For wheat, seeds (Limagrain, INTRO) were sterilized with an ethanol/bleach procedure and inoculated for 3 h on a shaker in the bacterial and mock solution. After 3 h inoculation, mock and inoculated wheat seeds were transferred to falcons with soil. Four seeds are sown per falcon tube to ensure two plants per falcon. Remaining seedlings were removed. The trays were kept at 23 degrees, long day light regime and at humidity of 55%. Every week, the falcons receive 10 ml $H_2O$. Plants were evaluated after three weeks of growth for root and shoot fresh biomass weight.

Figure 6:
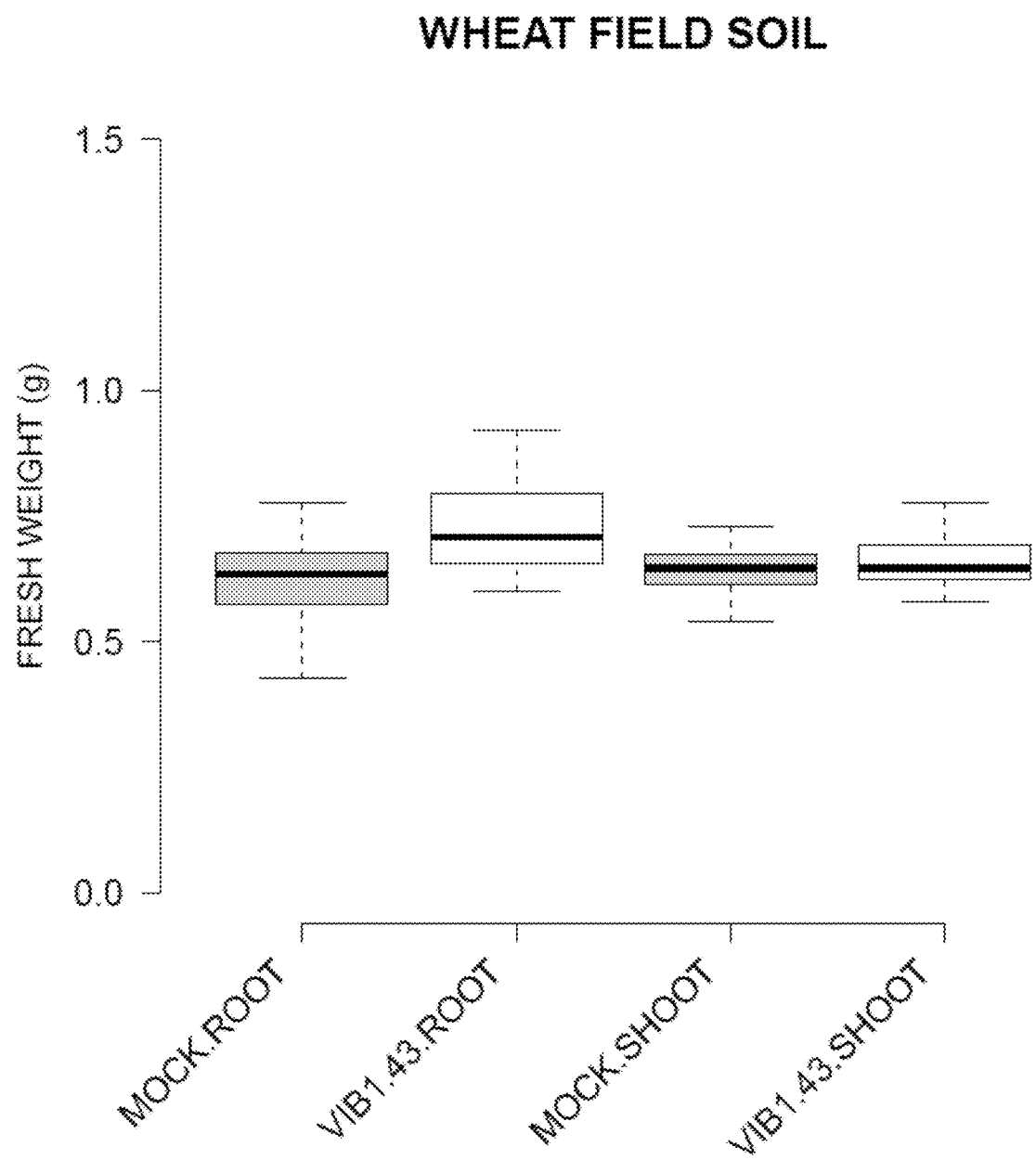

FIG. 6 shows merged data of two repeats of CA-227571 inoculated wheat seeds growing in field soil. A repeatable significant increase in the root fresh weight was observed. Root fresh weight of CA-227571 inoculated seed increased with 16% ($p<0.01$).

Example 5: DNA Extraction, Sequencing and Taxonomy of CA-227571

In order to taxonomically identify strain CA-227571, the 16S rDNA was sequenced. The 16S ribosomal gene (SEQ ID N° 1) has been amplified with the primer combination 27F/1492R amplifying a fragment of 1465 bp (Galkiewicz & Kellogg 2008, Applied and Environmental Microbiology 74: 7828-7831). A nucleotide blast using EzTaxon (http://www.ezbiocloud.net/eztaxon/identify) indicated the highest identity hits (99.06) to *Streptomyces niveus* strain NRRL 2466. The strain CA-227571 has been deposited with accession number: *Streptomyces niveus* CA-227571=LMG P-29828.

Example 6: Performance of CB-278407 Coated Maize Plants in Soil

In the next step, the effect of CB-278407 inoculation was tested on maize plants grown in poor soil conditions. Maize hybrid seeds (Limagrain, LG30.218) were sterilized with an ethanol/bleach procedure and germinated on $H_2O$+AGAR plates. Equally germinated seedlings after 48 h were selected for bacterial inoculation and mock inoculation. Seedlings were inoculated for 3 h on a shaker in the bacterial and mock solution. The growth of the maize seedlings was analyzed on the Phenovision platform. Therefore, 19 Phenovision pots are filled with an equal amount of soil (700 g). For this assay, we used a commercial soil, low in N and frequently used for research purposes. After 3 h inoculation, mock and inoculated seedlings were transferred to the pots with soil. Humidity was maintained on the platform to a constant level, pots were weighed every day on the automatic Phenovision platform and watered to a desired soil humidity of 2.4 (g $H_2O$/g dried soil). Plants were evaluated after three weeks of growth for root and shoot fresh biomass weight, leaf 3 and leaf 4 leaf length.

Figure 7:
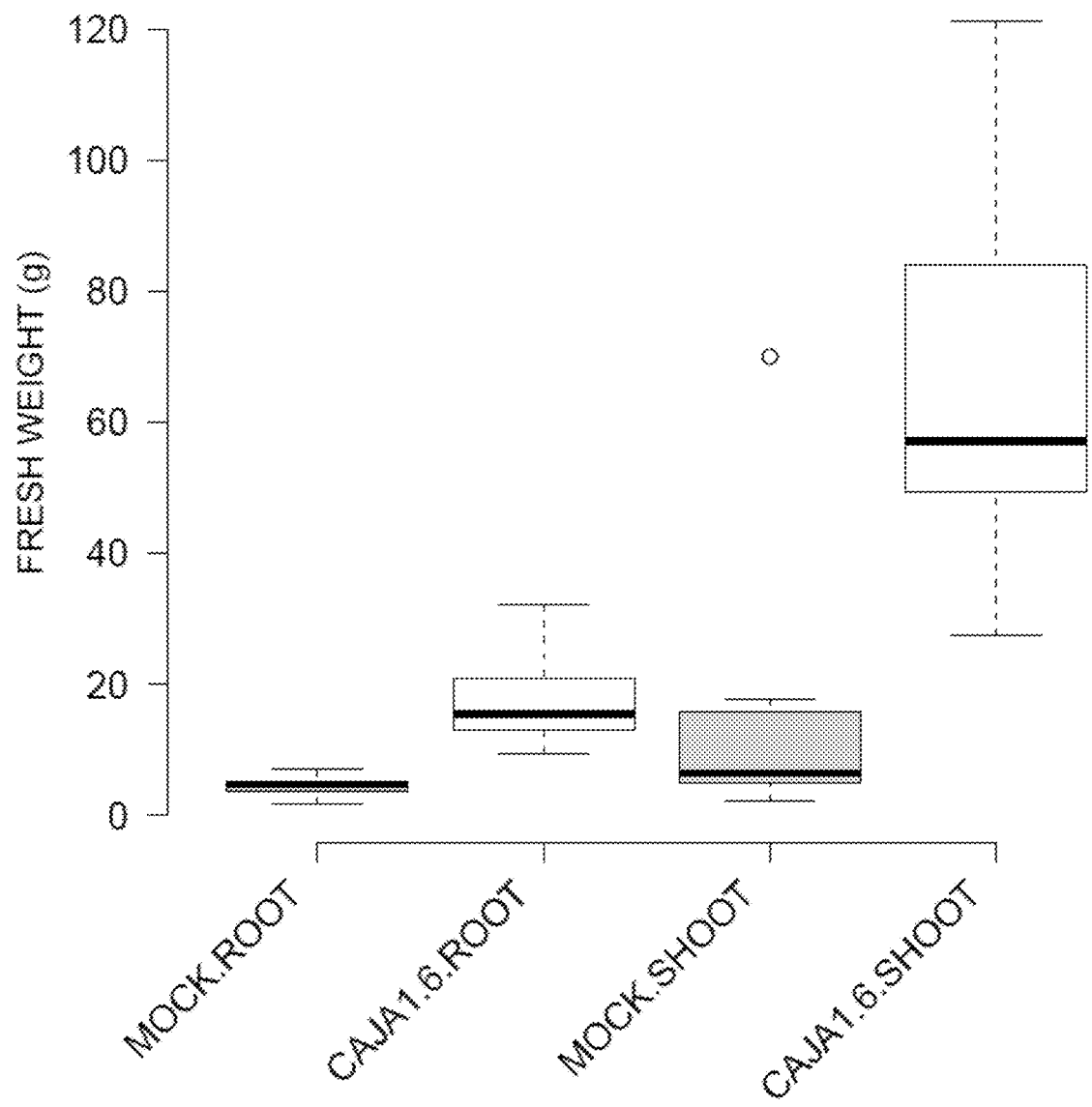
Figure 8:
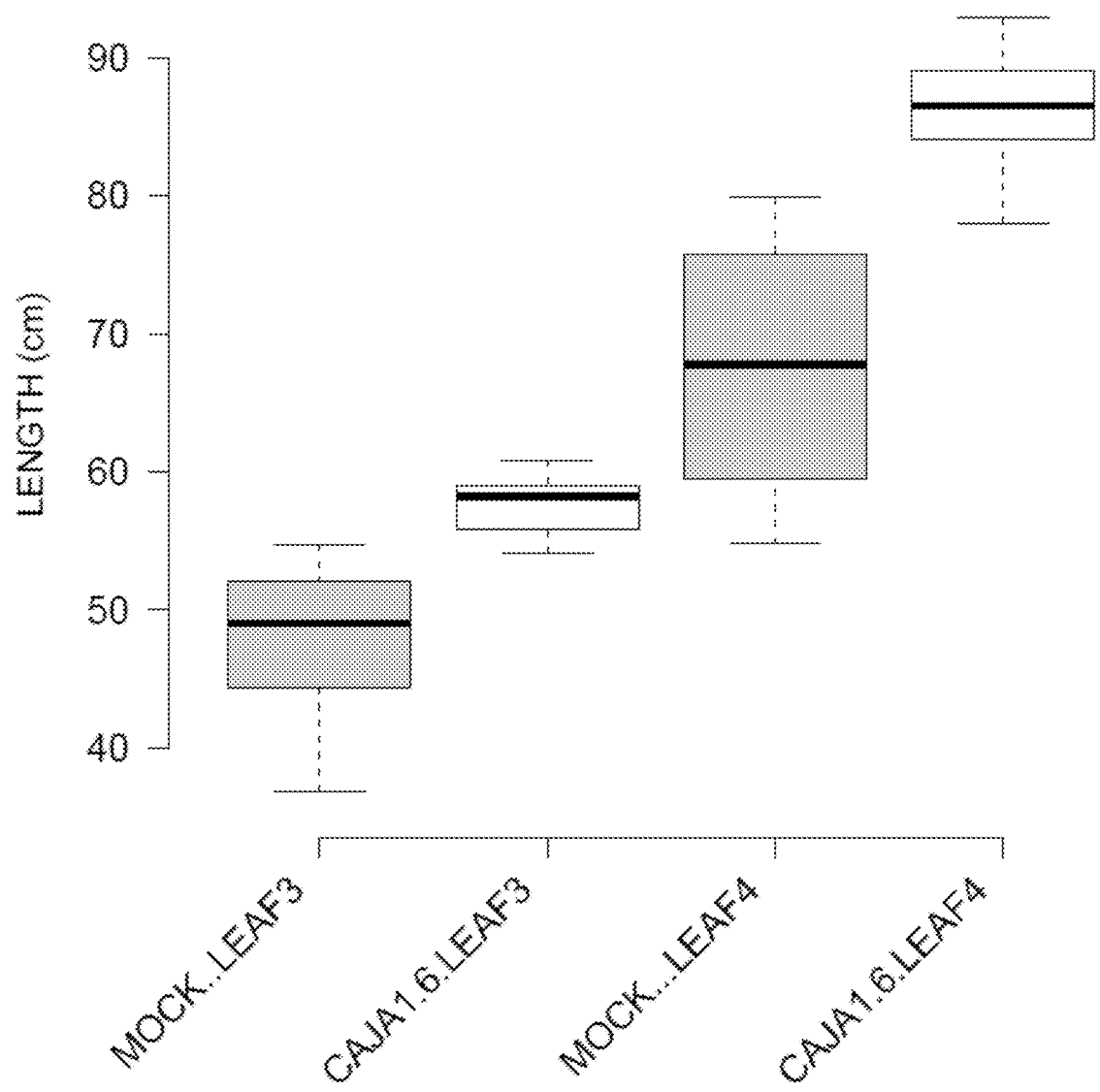

FIG. 7 shows the results for fresh root and shoot weight in the Phenovision screening. A significant increase in the root fresh weight was observed for the CB-278407 inoculated maize seedlings. CB-278407 inoculated maize seedlings showed a 291% increase in root fresh weight ($p<0.01$), while CB-278407 inoculation resulted in shoot fresh weight of 465% ($p<0.01$). FIG. 8 shows the results for the length of leaf 3 and leaf 4 in the Phenovision screening. For CB-278407 inoculation, we have observed a significant increase in length of both leaf 3 and leaf 4. Leaf 3 length increases with 21% for CB-278407 ($p<0.01$), while leaf 4 length increases with 27% for CB-278407 ($p<0.01$).

Example 7: Performance of CB-278407 Coated Wheat Seeds in Soil

In the final step, CB-278407 was tested for growth promotion on wheat juvenile growth. 20 falcon tubes were filled with an equal amount (80 g) of field soil (see Example 6) and watered with 10 ml $H_2O$. For wheat, seeds (Limagrain, INTRO) were sterilized with an ethanol/bleach procedure and inoculated for 3 h on a shaker in the bacterial and mock solution. After 3 h inoculation, mock and inoculated wheat seeds were transferred to falcons with soil. Four seeds are sown per falcon tube to ensure two plants per falcon. Remaining seedlings were removed. The trays were kept at 23 degrees, long day light regime and at humidity of 55%. Every week, the falcons receive 10 ml $H_2O$. Plants were evaluated after three weeks of growth for root and shoot fresh biomass weight.

Figure 9:
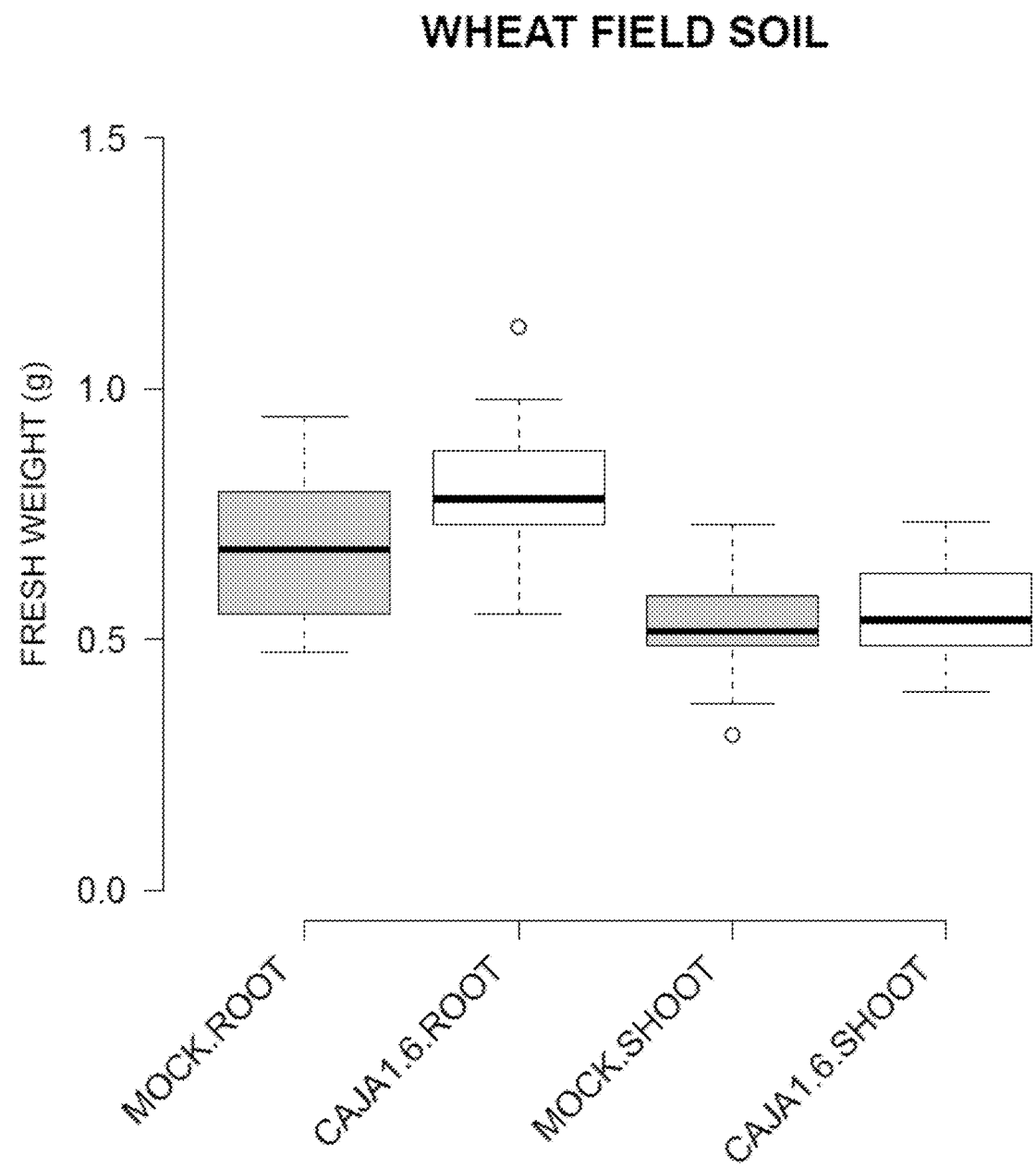

FIG. 9 shows merged data of two repeats of CB-278407 inoculated wheat seeds growing in field soil. A repeatable significant increase in the root fresh weight was observed. Root fresh weight of CB-278407 inoculated seed increased with 16% ($p<0.01$).

Example 8: DNA Extraction, Sequencing and Taxonomy of CB-278407

In order to taxonomically identify strain CB-278407, 16S rDNA was sequenced. The 16S ribosomal gene (SEQ ID N° 2) has been amplified with the primer combination 27F/1492R amplifying a fragment of 1465 bp (Galkiewicz & Kellogg, 2008). A nucleotide blast against the NCBI database indicated 100% identity to *Arthrobacter oxydans*. The strain CB-278407 has been deposited with accession number: *Arthrobacter oxydans* CB-278407=LMG P-29827.

Example 9: Plant Growth Promoting Effect of the Combination of CA-227571 and CB-278407 (*Streptomycves niveus* and *Arthrobacter Oxydans*)

The effect of a combination of CA-227571 and CB-278407 on wheat seedlings was tested. 20 falcon tubes were filled with an equal amount (80 g) of field soil (see Example 3 and 6) and watered with 10 ml $H_2O$. The wheat seeds (Limagrain, INTRO) were sterilized with an ethanol/bleach procedure and inoculated for 3 h on a shaker in the bacterial (CA-227571 and CB-278407) and mock solution. After 3 h inoculation, mock and inoculated wheat seeds were transferred to falcons with soil. Four seeds were sown per falcon tube to ensure two plants per falcon. Remaining seedlings were removed. The trays were kept at 23 degrees, long day light regime and at humidity of 55%. Every week, the falcons received 10 ml $H_2O$. Plants were evaluated after three weeks of growth for root and shoot fresh biomass weight.

Figure 10:
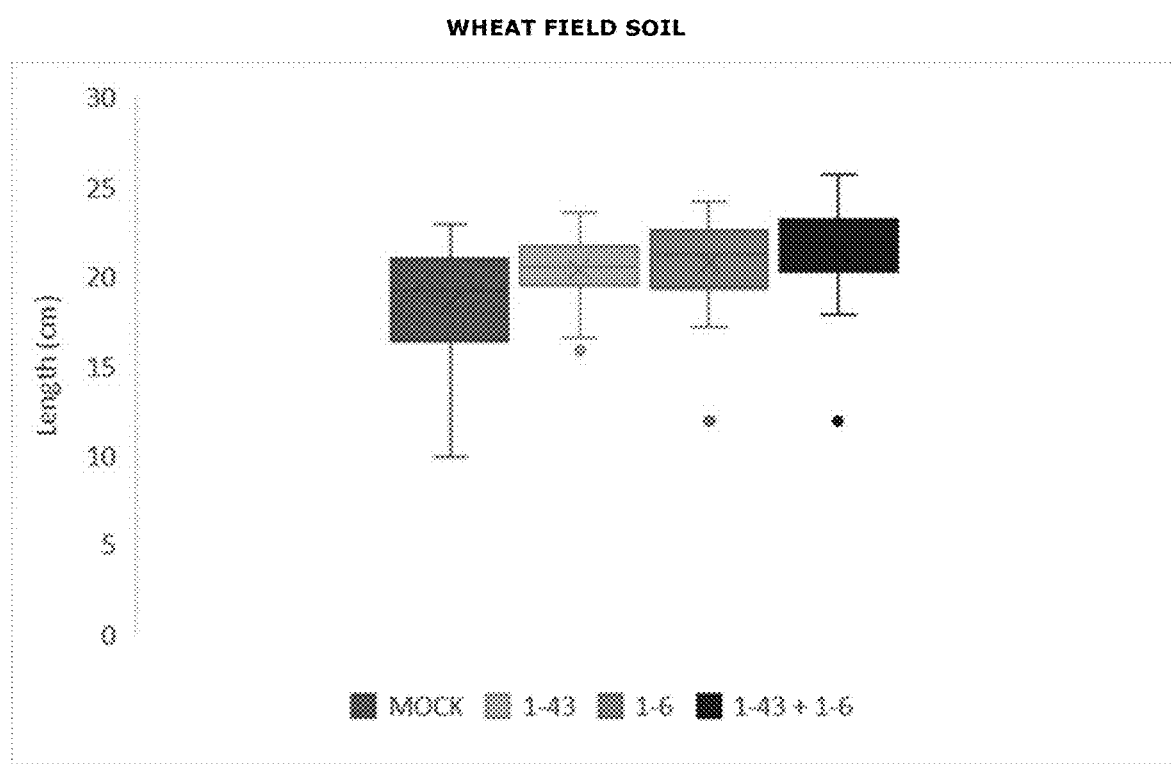

FIG. 10 shows the data of wheat seeds growing in field soil inoculated with CA-227571, CB-278407 and the combination of the two strains CA-227571 (1.43, *S. niveus*) and CB-278407 (1.6, *A. oxydans*) (20 repeats/treatment). A significant increase in leaf length of the second leaf was observed. Leaf 2 length of CA-227571 inoculated seed increased with 12% ($p<0.01$), Leaf 2 length of CB-278407 inoculated seed increased with 10% ($p<0.01$) and Leaf 2 length of CA-227571+CB-278407 inoculated seed increased with 15.5% ($p<0.01$). A combination of *S. niveus* and *A. oxydans* leads to a synergistic effect on plant growth.

Example 10: Plant Growth Promoting Effect of the Combination of CA-227571 (*Streptomyces niveus*) and CB-283399 (*Arthrobacter agilis*)

Finally, the effect of a combination of CA-227571 and CB-283399 was tested. Wheat seeds (Limagrain, INTRO) were inoculated for 3 h on a shaker in the bacterial (CA-227571 and CB-283399) and mock (no bacteria) solution before sowing them to a wheat greenhouse soil. The wheat greenhouse soil mixture consisted of 1:5 potting soil:propagation soil ratio, saturated with water. Subsequently, 20 plastic pots were filled with an equal amount of the 1:5 wheat greenhouse soil mixture. Mock and inoculated seeds were planted to the pots the 1:5 wheat greenhouse soil mixture. The trays were kept at 21° C. day temperature, 15° C. night temperature, with 12 hours light and 12 hours dark regime and humidity of 75%. Plants were evaluated every week for plant heights (weeks 2-5) and harvested after seven weeks for dry weight shoot biomass determination.

Figure 11:
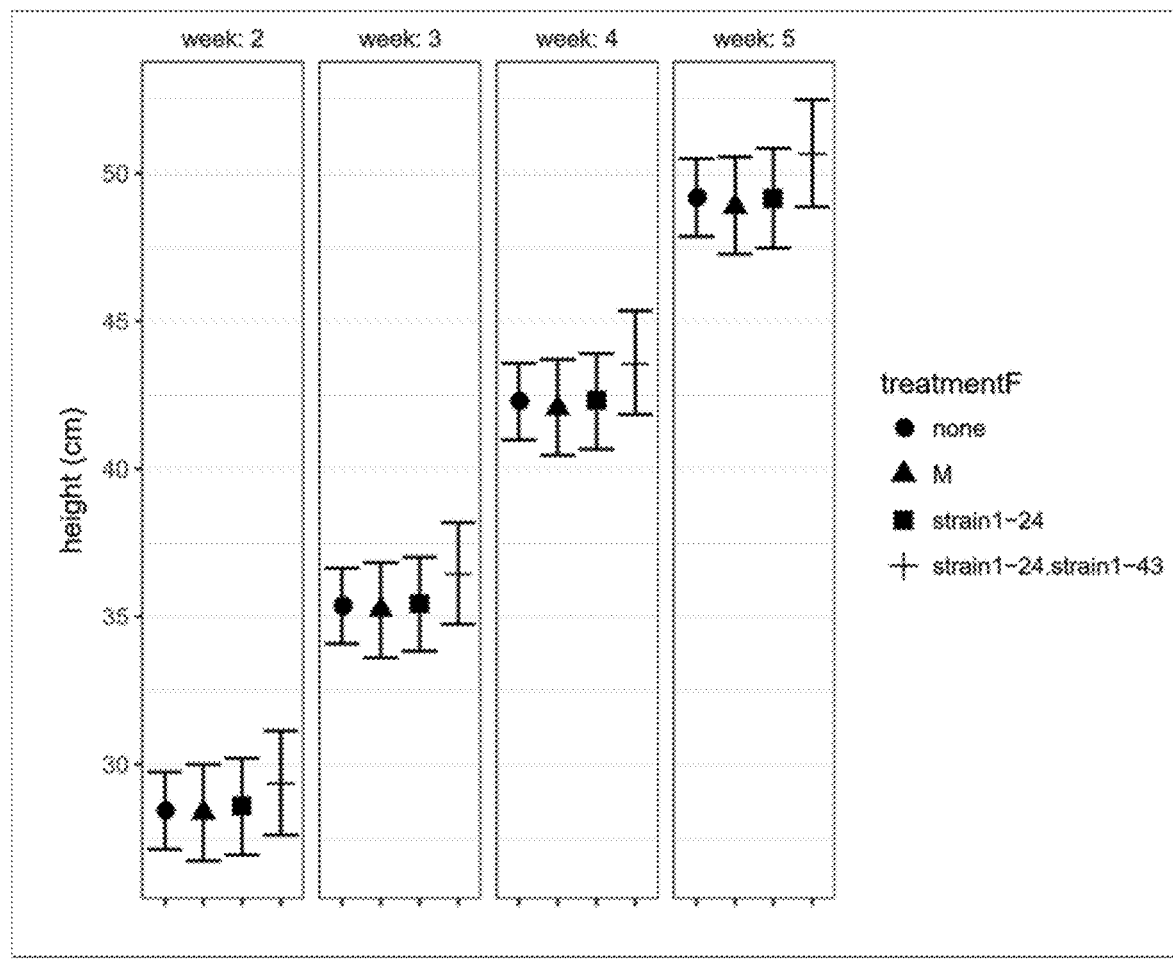
Figure 12:
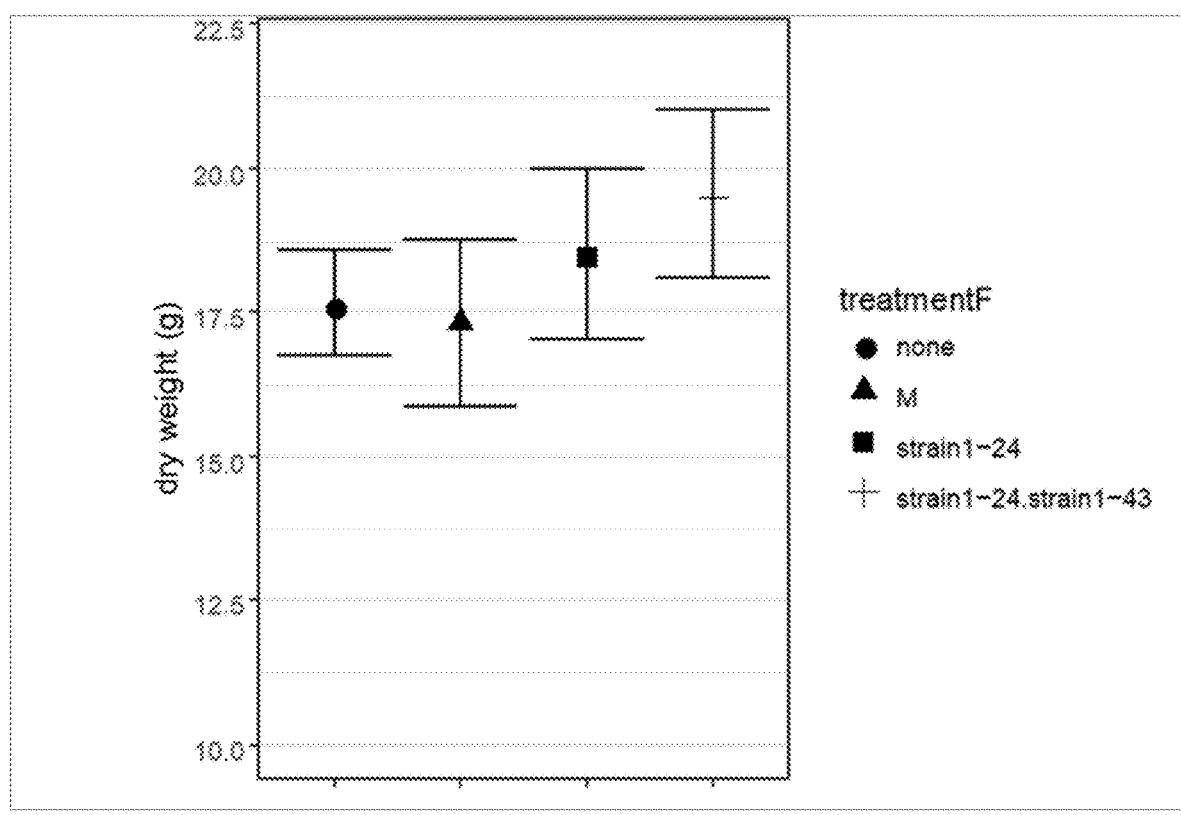

FIG. 11 shows a significant increase in plant height of 4% at weeks 2-5 for the combination of CA-227571 and CB-283399 (strain 1-24 and 1-43; *Streptomyces niveus* and *Arthrobacter agilis*). FIG. 12 shows a significant increase in dry weight biomass of 12% at week 7 for the combination of CA-227571 and CB-283399 (strain 1-24 and 1-43; *Streptomyces niveus* and *Arthrobacter agilis*). A combination of *S. niveus* and *A. agilis* leads to a synergistic effect on plant growth.

Example 11: DNA Extraction, Sequencing and Taxonomy of CB-283399

In order to taxonomically identify strain CB-283399, 16S rDNA was sequenced. The 16S ribosomal gene (SEQ ID N°

3) has been amplified with the primer combination with the primer combination 27F/1492R amplifying a fragment of 1395 bp (Galkiewicz & Kellogg, 2008). A nucleotide blast against the NCBI database indicated 100% identity to *Arthrobacter agilis*.

(16S rRNA from *Streptomyces niveus* CA-227571)
SEQ ID No 1
AGTCGAACGATGAAGCCTTCGGGTGGATTAGTGGCGAACGGGTGAGTAAC
ACTGTGGGCAATCTGCCCTGCACTCTGGGACAAGCCCTGGAAACGGGGTC
TAATACCGGATAATACTGTGCCCCTCCTGGGGGACGGTTGAAAGCTCCGG
CGGTGCAGGATGAGCCCGCGGCCTATCAGCTTGTTGGTGGGGTAATGGCC
TACCAAGGCGACGACGGGTAGCCGGCCTGAGAGGGCGACCGGCCACACTG
GGACTGAGACACGGCCCAGACTCCTACGGGAGGCAGCAGTGGGGAATATT
GCACAATGGGCGAAAGCCTGATGCAGCGACGCCGCGTGAGGGATGACGGC
CTTCGGGTTGTAAACCTCTTTCAGCAGGGAAGAAGCGAAAGTGACGGTAC
CTGCAGAAGAAGCGCCGGCTAACTACGTGCCAGCAGCCGCGGTAATACGT
AGGGCGCAAGCGTTGTCCGGAATTATTGGGCGTAAAGAGCTCGTAGGCGG
TTTGTCACGTCGGGTGTGAAAGCCCGGGGCTTAACCCCGGGTCTGCATTC
GATACGGGCAGACTAGAGTGTGGTAGGGGAGATCGGAATTCCTGGTGTAG
CGGTGAAATGCGCAGATATCAGGAGGAACACCGGTGGCGAAGGCGGATCT
CTGGGCCATTACTGACGCTGAGGAGCGAAAGCGTGGGGAGCGAACAGGAT
TAGATACCCTGGTAGTCCACGCCGTAAACGTTGGGAACTAGGTGTTGGCG
ACATTCCACGTCGTCGGTGCCGCAGCTAACGCATTAAGTTCCCCGCCTGG
GGAGTACGGCCGCAAGGCTAAAACTCAAAGGAATTGACGGGGCCCGCAC
AAGCAGCGGAGCATGTGGCTTAATTCGACGCAACGCGAAGAACCTTACCA
AGGCTTGACATACACCGGAAAGCATCAGAGATGGTGCCCCCCTTGTGGTC
GGTGTACAGGTGGTGCATGGCTGTCGTCAGCTCGTGTCGTGAGATGTTGG
GTTAAGTCCCGCAACGAGCGCAACCCTTGTTCTGTGTTGCCAGCATGCCT
TTCGGGGTGATGGGGACTCACAGGAGACCGCCGGGGTCAACTCGGAGGAA
GGTGGGGACGACGTCAAGTCATCATGCCCCTTATGTCTTGGGCTGCACAC
GTGCTACAATGGCCGGTACAATGAGCTGCGATACCGCAAGGTGGAGCGAA
TCTCAAAAAGCCGGTCTCAGTTCGGATTGGGGTCTGCAACTCGACCCCAT
GAAGTCGGAGTTGCTAGTAATCGCAGATCAGCATTGCTGCGGTGAATACG
TTCCCGGGCCTTGTACACACCGCCCGTCTAGTGGCGAAAGTCGGTAACAC
CCGAAGCCGGTGGCCCAACCCCTTGGGAGGGAG (16S rRNA from *Arthrobacter oxydans* CB-278407)
SEQ ID No 2
TGCAAGTCGAACGATGATCCGGTGCTTGCACCGGGGATTAGTGGCGAACG
GGTGAGTAACACGTGAGTAACCTGCCCTTAACTCTGGGATAAGCCTGGGA
AACTGGGTCTAATACCGGATATGACTGATCATCGCATGGTGGTTGGTGGA
AAGCTTTTTGTGGTTTTGGATGGACTCGCGGCCTATCAGCTTGTTGGTGA
GGTAATGGCTTACCAAGGCGACGACGGGTAGCCGGCCTGAGAGGGTGACC
GGCCACACTGGGACTGAGACACGGCCCAGACTCCTACGGGAGGCAGCAGT
GGGGAATATTGCACAATGGGCGCAAGCCTGATGCAGCGACGCCGCGTGAG
GGATGACGGCCTTCGGGTTGTAAACCTCTTTCAGTAGGGAAGAAGCGAAA
GTGACGGTACCTGCAGAAGAAGCGCCGGCTAACTACGTGCCAGCAGCCGC
GGTAATACGTAGGGCGCAAGCGTTATCCGGAATTATTGGGCGTAAAGAGC
TCGTAGGCGGTTTGTCGCGTCTGCCGTGAAAGTCCGGGGCTCAACTCCGG
ATCTGCGGTGGGTACGGGCAGACTAGAGTGATGTAGGGGAGACTGGAATT
CCTGGTGTAGCGGTGAAATGCGCAGATATCAGGAGGAACACCGATGGCGA
AGGCAGGTCTCTGGGCATTAACTGACGCTGAGGAGCGAAAGCATGGGGAG
CGAACAGGATTAGATACCCTGGTAGTCCATGCCGTAAACGTTGGGCACTA
GGTGTGGGGGACATTCCACGTTTTCCGCGCCGTAGCTAACGCATTAAGTG
CCCCGCCTGGGGAGTACGGCCGCAAGGCTAAAACTCAAAGGAATTGACGG
GGGCCCGCACAAGCGGCGGAGCATGCGGATTAATTCGATGCAACGCGAAG
AACCTTACCAAGGCTTGACATGAACCGGAAAGACCTGGAAACAGGTGCCC
CGCTTGCGGTCGGTTTACAGGTGGTGCATGGTTGTCGTCAGCTCGTGTCG
TGAGATGTTGGGTTAAGTCCCGCAACGAGCGCAACCCTCGTTCTATGTTG
CCAGCACGTGATGGTGGGGACTCATAGGAGACTGCCGGGGTCAACTCGGA
GGAAGGTGGGGACGACGTCAAATCATCATGCCCCTTATGTCTTGGGCTTC
ACGCATGCTACAATGGCCGGTACAAAGGGTTGCGATACTGTGAGGTGGAG
CTAATCCCAAAAAGCCGGTCTCAGTTCGGATTGGGGTCTGCAACTCGACC
CCATGAAGTCGGAGTCGCTAGTAATCGCAGATCAGCAACGCTGCGGTGAA
TACGTTCCCGGGCCTTGTACACACCGCCCGTCAAGTCACGAAAGTTGGTA
ACACCCGAAGCCGGTGGCCTAACCCCTTGTGGGAGGGA (16S rRNA from *Arthrobacter agilis*)
SEQ ID No 3
TTCGACGGCTCCCTCCCACAAGGGGTTAGGCCACCGGCTTCGGGTGTTAC
CAACTTTCGTGACTTGACGGGCGGTGTGTACAAGGCCCGGGAACGTATTC
ACCGCAGCGTTGCTGATCTGCGATTACTAGCGACTCCAACTTCATGAGGT
CGAGTTGCAGACCTCAATCCGAACTGAGACCGGCTTTTTGGGATTAGCTC
CACCTCACAGTATCGCAACCCTTTGTACCGGCCATTGTAGCATGCGTGAA
GCCCAAGACATAAGGGGCATGATGATTTGACGTCGTCCCCACCTTCCTCC
GAGTTGACCCCGGCAGTCTCCCATGAGTCCCGGCATAACCCGCTGGCAA
CATGGAACGAGGGTTGCGCTCGTTGCGGGACTTAACCCAACATCTCACGA
CACGAGCTGACGACAACCATGCACCACCTGTAAACCGGCCACAAGTGGCT
GACGCATCTCTGCGCCATTCCGGTTCATGTCAAGCCTTGGTAAGGTTCTT
CGCGTTGCATCGAATTAATCCGCATGCTCCGCCGCTTGTGCGGGCCCCCG
TCAATTCCTTTGAGTTTTAGCCTTGCGGCCGTACTCCCCAGGCGGGGCAC
TTAATGCGTTAGCTACGGCGCGGAAAACGTGGAATGTCCCCCACACCTAG
TGCCCAACGTTTACGGCATGGACTACCAGGGTATCTAATCCTGTTCGCTC
CCCATGCTTTCGCTCCTCAGCGTCAGTTACAGCCCAGAGACCTGCCTTCG
CCATCGGTGTTCCTCCTGATATCTGCGCATTTCACCGCTACACCAGGAAT
TCCAGTCTCCCCTACTGCACTCTAGTCTGCCCGTACCCACCGCAGATCCG
GAGTTAAGCCCCGGACTTTCACGGCAGACGCGACAAACCGCCTACGAGCT
CTTTACGCCCAATAATTCCGGATAACGCTTGCGCCCTACGTATTACCGCG -continued

GCTGCTGGCACGTAGTTAGCCGGCGCTTCTTCTGCAGGTACCGTCACTTT

CGCTTCTTCCCTACTGAAAGAGGTTTACAACCCGAAGGCCTTCATCCCTC

ACGCGGCGTCGCTGCATCAGGCTTGCGCCCATTGTGCAATATTCCCCACT

GCTGCCTCCCGTAGGAGTCTGGGCCGTGTCTCAGTCCCAGTGTGGCCGGT

-continued

CACCCTCTCAGGCCGGCTACCCGTCGTCGCCTTGGTGGGCCATTACCCCG

CCAACAAGCTGATAGGCCGCGAGTCCATCCAAAACCGCAATAAAGCTTTC

CACCACCAGGCCATGCGGCCGGCAGTCATATCCGGTATTAGACCCGGTTT

CCCAGGCTTATCCCAGAGTCAAGGGCAGGTTACTCACGTGTTACTCACCC

GTTCGCCACTAATCCACCAGCAAGCTGGCTTCATCGTTCGACTGC

---

What is claimed is:

1. A method for enhancing growth and/or yield of a plant comprising:
   inoculating a plant growth medium with a microbial population, wherein said population comprises a bacterial strain comprising a 16S rRNA sequence exhibiting at least 99.1% sequence identity to SEQ ID No: 1; growing a plant in said plant growth medium; to enhance growth and/or yield of said plant.

2. The method of claim 1, comprising growing a plant in the said plant growth medium to increase nutrient uptake and/or nutrient use efficiency of the plant.

3. The method of claim 1, comprising growing a plant in the said plant growth medium to increase the nitrogen fixating capacities of the plant.

4. The method of claim 1, wherein the microbial population is applied to the plant growth medium as a powder, as a pellet, as a granule, as a liquid.

5. A method for enhancing growth and/or yield of a plant, said method comprising growing coated seeds of a plant, wherein said seeds are coated with an agricultural composition comprising a bacterial strain comprising a 16S rRNA sequence exhibiting at least 99.1% sequence identity to SEQ ID No: 1 and an agriculturally compatible carrier, thereby obtaining enhanced growth and/or yield of said plant.

6. A method for enhancing growth and/or yield of a plant comprising:
   growing a plant in an environment that supports plant growth;
   administering a sprayable formulation to said environment or to said plant, said formulation comprising the agricultural composition comprising a bacterial strain comprising a 16S rRNA sequence exhibiting at least 99.1% sequence identity to SEQ ID No: 1 and an agriculturally compatible carrier;
   thereby obtaining enhanced growth and/or yield of said plant.

* * * * *

SEQUENCE LISTING

<160> NUMBER OF SEQ ID NOS: 3

<210> SEQ ID NO 1
<211> LENGTH: 1384
<212> TYPE: DNA
<213> ORGANISM: Streptomyces niveus

<400> SEQUENCE: 1

```
agtcgaacga tgaagccttc gggtggatta gtggcgaacg ggtgagtaac actgtgggca      60
atctgccctg cactctggga caagccctgg aaacggggtc taataccgga taatactgtg     120
cccctcctgg gggacggttg aaagctccgg cggtgcagga tgagcccgcg gcctatcagc     180
ttgttggtgg ggtaatggcc taccaaggcg acgacgggta gccggcctga gagggcgacc     240
ggccacactg gactgagaca cggcccagac tcctacggga aggcagcagt ggggaatatt     300
gcacaatggg cgaaagcctg atgcagcgac gccgcgtgag ggatgacggc cttcggttg     360
taaacctctt tcagcaggga agaagcgaaa gtgacggtac ctgcagaaga agcgccggct     420
aactacgtgc cagcagccgc ggtaatacgt agggcgcaag cgttgtccgg aattattggg     480
cgtaaagagc tcgtaggcgg tttgtcacgt cgggtgtgaa agcccgggc ttaaccccgg      540
gtctgcattc gatacgggca gactagagtg tggtagggga gatcggaatt cctggtgtag     600
cggtgaaatg cgcagatatc aggaggaaca ccggtggcga aggcggatct ctgggccatt     660
actgacgctg aggagcgaaa gcgtggggag cgaacaggat tagataccct ggtagtccac     720
gccgtaaacg ttgggaacta ggtgttggcg acattccacg tcgtcggtgc cgcagctaac     780
gcattaagtt ccccgcctgg ggagtacggc cgcaaggcta aaactcaaag gaattgacgg     840
gggcccgcac aagcagcgga gcatgtggct taattcgacg caacgcgaag aaccttacca     900
aggcttgaca tacaccggaa agcatcagag atggtgcccc ccttgtggtc ggtgtacagg     960
tggtgcatgg ctgtcgtcag ctcgtgtcgt gagatgttgg gttaagtccc gcaacgagcg    1020
caacccttgt tctgtgttgc cagcatgcct ttcggggtga tggggactca caggagaccg    1080
ccggggtcaa ctcggaggaa ggtgggacg acgtcaagtc atcatgcccc ttatgtcttg    1140
ggctgcacac gtgctacaat ggccggtaca atgagctgcg ataccgcaag gtggagcgaa    1200
tctcaaaaag ccggtctcag ttcggattgg ggtctgcaac tcgacccat gaagtcggag    1260
ttgctagtaa tcgcagatca gcattgctgc ggtgaatacg ttcccgggcc ttgtacacac    1320
cgcccgtcta gtggcgaaag tcggtaacac ccgaagccgg tggcccaacc ccttggggag    1380
ggag                                                                 1384
```

<210> SEQ ID NO 2
<211> LENGTH: 1388
<212> TYPE: DNA
<213> ORGANISM: Arthrobacter oxydans

<400> SEQUENCE: 2

| | |
|---|---:|
| tgcaagtcga acgatgatcc ggtgcttgca ccggggatta gtggcgaacg ggtgagtaac | 60 |
| acgtgagtaa cctgcccctta actctgggat aagcctggga aactgggtct aataccggat | 120 |
| atgactgatc atcgcatggt ggttggtgga agcttttttg tggttttgga tggactcgcg | 180 |
| gcctatcagc ttgttggtga ggtaatggct taccaaggcg acgacgggta gccggcctga | 240 |
| gagggtgacc ggccacactg gactgagac acggcccaga ctcctacggg aggcagcagt | 300 |
| ggggaatatt gcacaatggg cgcaagcctg atgcagcgac gccgcgtgag ggatgacggc | 360 |
| cttcggggttg taaacctctt tcagtaggga agaagcgaaa gtgacggtac ctgcagaaga | 420 |
| agcgccggct aactacgtgc cagcagccgc ggtaatacgt agggcgcaag cgttatccgg | 480 |
| aattattggg cgtaaagagc tcgtaggcgg tttgtcgcgt ctgccgtgaa agtccggggc | 540 |
| tcaactccgg atctgcggtg ggtacgggca gactagagtg atgtagggga gactggaatt | 600 |
| cctggtgtag cggtgaaatg cgcagatatc aggaggaaca ccgatggcga aggcaggtct | 660 |
| ctgggcatta actgacgctg aggagcgaaa gcatggggag cgaacaggat tagataccct | 720 |
| ggtagtccat gccgtaaacg ttgggcacta ggtgtggggg acattccacg ttttccgcgc | 780 |
| cgtagctaac gcattaagtg ccccgcctgg ggagtacggc cgcaaggcta aaactcaaag | 840 |
| gaattgacgg gggcccgcac aagcggcgga gcatgcggat taattcgatg caacgcgaag | 900 |
| aaccttacca aggcttgaca tgaaccggaa agacctggaa acaggtgccc cgcttgcggt | 960 |
| cggtttacag tggtgcatg gttgtcgtca gctcgtgtcg tgagatgttg ggttaagtcc | 1020 |
| cgcaacgagc gcaaccctcg ttctatgttg ccagcacgtg atggtgggga ctcataggag | 1080 |
| actgccgggg tcaactcgga ggaaggtggg gacgacgtca atcatcatg ccccttatgt | 1140 |
| cttgggcttc acgcatgcta caatggccgg tacaaagggt tgcgatactg tgaggtggag | 1200 |
| ctaatcccaa aaagccggtc tcagttcgga ttggggtctg caactcgacc ccatgaagtc | 1260 |
| ggagtcgcta gtaatcgcag atcagcaacg ctgcggtgaa tacgttcccg ggccttgtac | 1320 |
| acaccgcccg tcaagtcacg aaagttggta acacccgaag ccggtggcct aaccccttgt | 1380 |
| gggaggga | 1388 |

```
<210> SEQ ID NO 3
<211> LENGTH: 1395
<212> TYPE: DNA
<213> ORGANISM: Arthrobacter agilis

<400> SEQUENCE: 3
```

| | |
|---|---:|
| ttcgacggct ccctcccaca aggggttagg ccaccggctt cgggtgttac caactttcgt | 60 |
| gacttgacgg gcggtgtgta caaggcccgg gaacgtattc accgcagcgt tgctgatctg | 120 |
| cgattactag cgactccaac ttcatgaggt cgagttgcag acctcaatcc gaactgagac | 180 |
| cggcttttttg ggattagctc cacctcacag tatcgcaacc ctttgtaccg gccattgtag | 240 |
| catgcgtgaa gcccaagaca taaggggcat gatgatttga cgtcgtcccc accttcctcc | 300 |
| gagttgaccc cggcagtctc ccatgagtcc ccggcataac ccgctggcaa catgaacga | 360 |
| gggttgcgct cgttgcggga cttaacccaa catctcacga cacgagctga cgacaaccat | 420 |
| gcaccacctg taaccggcc acaagtggct gacgcatctc tgcgccattc cggttcatgt | 480 |
| caagccttgg taaggttctt cgcgttgcat cgaattaatc cgcatgctcc gccgcttgtg | 540 |
| cgggccccccg tcaattcctt tgagttttag ccttgcggcc gtactcccca ggcggggcac | 600 |
| ttaatgcgtt agctacggcg cggaaaacgt ggaatgtccc ccacacctag tgcccaacgt | 660 |
| ttacggcatg gactaccagg gtatctaatc ctgttcgctc cccatgcttt cgctcctcag | 720 |

```
cgtcagttac agcccagaga cctgccttcg ccatcggtgt tcctcctgat atctgcgcat      780
ttcaccgcta caccaggaat tccagtctcc cctactgcac tctagtctgc ccgtacccac      840
cgcagatccg gagttaagcc ccggactttc acggcagacg cgacaaaccg cctacgagct      900
ctttacgccc aataattccg gataacgctt gcgccctacg tattaccgcg gctgctggca      960
cgtagttagc cggcgcttct tctgcaggta ccgtcacttt cgcttcttcc ctactgaaag     1020
aggtttacaa cccgaaggcc ttcatccctc acgcggcgtc gctgcatcag gcttgcgccc     1080
attgtgcaat attccccact gctgcctccc gtaggagtct gggccgtgtc tcagtcccag     1140
tgtggccggt caccctctca ggccggctac ccgtcgtcgc cttggtgggc cattaccccg     1200
ccaacaagct gataggccgc gagtccatcc aaaaccgcaa taaagctttc caccaccagg     1260
ccatgcggcc ggcagtcata tccggtatta gacccggttt cccaggctta tcccagagtc     1320
aagggcaggt tactcacgtg ttactcaccc gttcgccact aatccaccag caagctggct     1380
tcatcgttcg actgc                                                      1395
```